(12) United States Patent
Evans et al.

(10) Patent No.: US 8,101,714 B2
(45) Date of Patent: Jan. 24, 2012

(54) TELEOST DERIVED ANTIMICROBIAL POLYPEPTIDES

(75) Inventors: Donald L. Evans, Athens, GA (US); Harjeet Kaur, DeForest, WI (US); Liliana Jaso-Friedmann, Athens, GA (US); John H. Leary, III, Athen, GA (US); Kesavannair Praveen, Aurora, IL (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 961 days.

(21) Appl. No.: 10/588,417

(22) PCT Filed: Feb. 18, 2005

(86) PCT No.: PCT/US2005/005398
§ 371 (c)(1),
(2), (4) Date: Apr. 7, 2008

(87) PCT Pub. No.: WO2005/079523
PCT Pub. Date: Sep. 1, 2005

(65) Prior Publication Data
US 2009/0311278 A1 Dec. 17, 2009

Related U.S. Application Data

(60) Provisional application No. 60/545,370, filed on Feb. 18, 2004, provisional application No. 60/623,909, filed on Nov. 1, 2004.

(51) Int. Cl.
*C07K 14/00* (2006.01)
(52) U.S. Cl. .................................................. 530/350

(58) Field of Classification Search .................. None
See application file for complete search history.

(56) References Cited

U.S. PATENT DOCUMENTS
6,884,423 B1 4/2005 Class et al.

OTHER PUBLICATIONS

Chenik, M, et al., (2006) "Vaccination with the divergent portion of the protein histone H2B of *Leishmania* protects susceptible BALB/c mice against a virulent challenge with *Leishmania major*" Vaccine 24:2521-2529.

*Primary Examiner* — Michael Pak
(74) *Attorney, Agent, or Firm* — Henry D. Coleman; R. Neil Sudol; William J. Sapone

(57) ABSTRACT

The invention is directed to an isolated polypeptide which (a) is obtainable from a teleost; (b) has antimicrobial activity; (c) binds to oligoguanosine and/or CpG (SEQ ID NO:7); (d) comprises 58 strongly basic amino acids selected from the group consisting of K and R; (e) comprises 50 hydrophobic amino acids selected from the group consisting of A, I, L, F, W and V; (f) comprises 50 polar amino acids selected from the group consisting of N, C, Q, S, T and Y and (g) contains 11 lysine-rich motifs and antimicrobial fragments thereof as well as methods for preparing said polypeptides, compositions and libraries comprising said polypeptide(s) and uses of said polypeptide(s), particularly in treating microbial infections. The invention is further directed to a nucleic acid(s) encoding said polypeptide, microarrays comprising said nucleic acid(s) and uses for said nucleic acid(s). Furthermore, the invention is directed to an antibody which birds to the polypeptide of the present invention and uses for said antibodies.

4 Claims, 17 Drawing Sheets

A

B dG20-Biotin (μg/ml)

Fold Excess Cold Competitor

Figures 4A - 4C
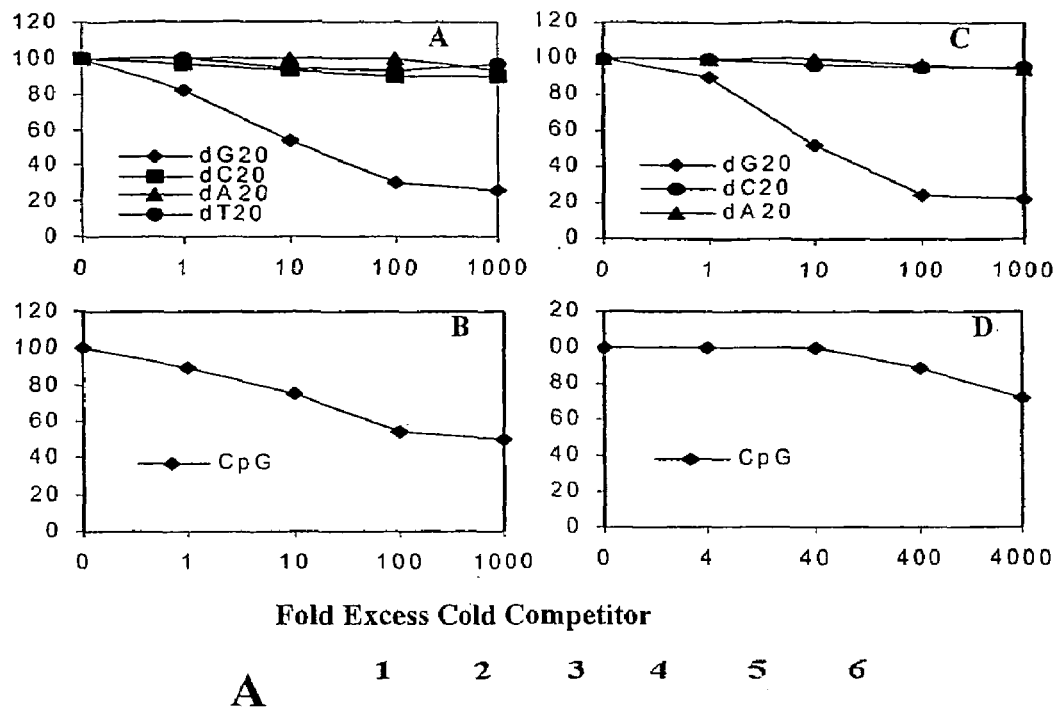
Fold Excess Cold Competitor
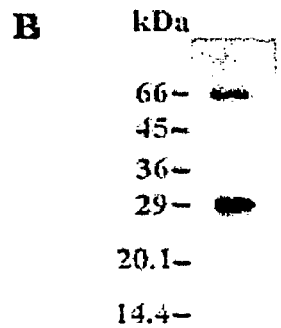
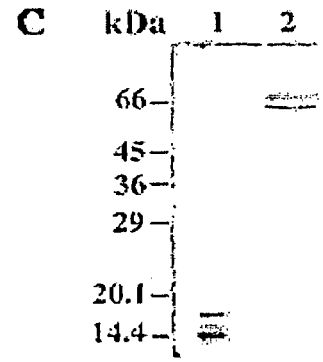

A

B

Figure 6
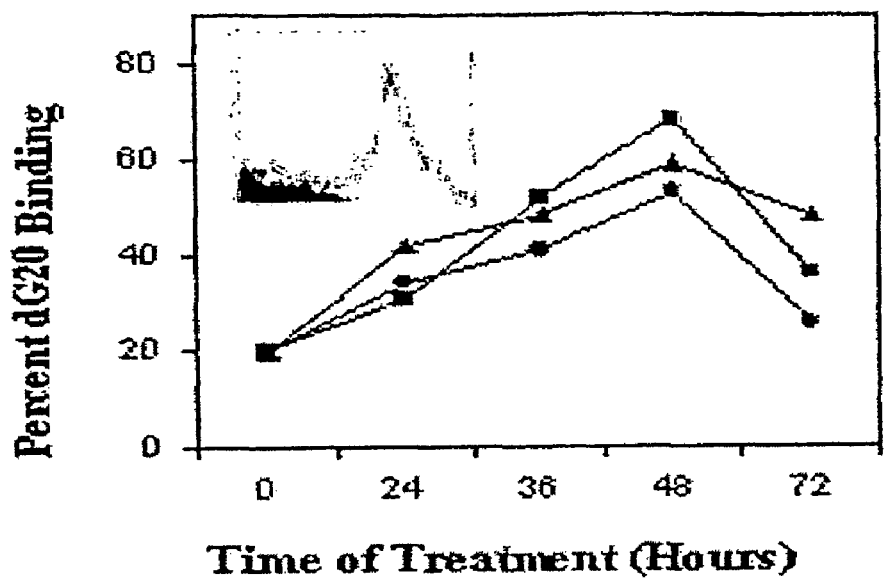
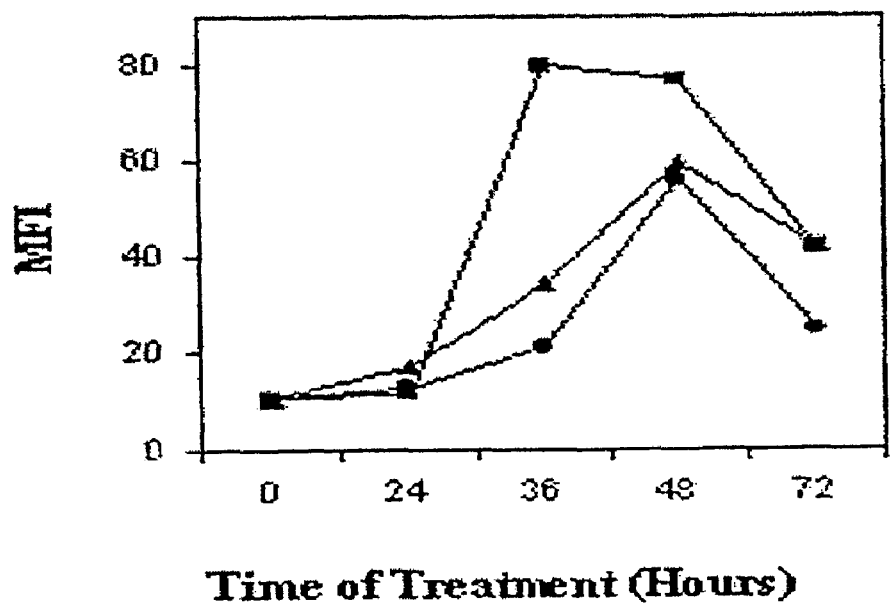

Figure 10

```
  1  CGGCACGAGGGTTCAATAGCATCTCAAGGCGCTTCAGAACTTAAAGTTGA
          M  S  A  Q  A  E  E  T  A  P  E  A  A  A  P  V    16
 51  ACCATGTCTGCTCAGGCTGAGGAAACTGCACCAGAAGCAGCAGCACCAGT
        Q  P  S  Q  P  A  A  K  K  K  G  P  A  S  K  A     32
101  ACAACCATCACAACCAGCGGCCAAAAAGAAGGGACCCGCCAGTAAAGCAA
        K  P  A  S  A  E  K  K  N  K  K  K  G  K  G  P     49
151  AGCCTGCCTCTGCAGAAAAAAGAACAAAAAGAAGAAAGGGAAAGGGCCC
           G  K  Y  S  Q  L  V  I  N  A  I  Q  T  L  G  E  R    66
201  GGAAAGTACAGCCAGCTGGTGATCAATGCTATCCAAACGCTGGGAGAGAG
           N  G  S  S  L  F  K  I  Y  N  E  A  K  K  V  N     82
251  AAACGGCTCGTCTCTTTTTAAGATCTACAACGAGGCGAAGAAAGTGAACT
           W  F  D  Q  Q  H  G  R  V  Y  L  R  Y  S  I  R  A    99
301  GGTTTGACCAGCAGCACGGGCGCGTGTACCTCCGCTACTCCATCCGCGCG
           L  L  Q  N  D  T  L  V  Q  V  K  G  L  G  A  N  G   116
351  CTGCTGCAGAACGACACGCTCGTGCAGGTGAAGGGTCTGGGCGCCAACGG
           S  F  K  L  N  K  K  F  I  P  R  T  K  K  S        132
401  CTCCTTCAAGCTCAACAAAAAGAAGTTCATCCCCAGAACCAAGAAGAGCT
           S  V  K  P  R  K  T  A  K  P  T  K  K  P  A  K  K   149
451  CTGTAAAGCCGAGAAAGACTGCGAAACCGACCAAAAAGCCAGCCAAAAAA
           A  A  K  K  K  K  R  V  S  G  V  K  K  A  T  P  P   166
501  GCAGCGAAGAAGAAGAAAAGGGTCAGCGGCGTGAAGAAGGCGACTCCCCC
              P  E  K  T  S  K  P  K  K  A  D  K  S  P  A  V  182
551  CCCAGAGAAAACCTCCAAACCCAAGAAAGCGGATAAAAGTCCAGCCGTCT
              S  A  K  K  A  S  K  P  K  K  A  Q  T  K  K  T  199
601  CTGCCAAGAAGGCGAGCAAGCCCAAGAAAGCTAAACAGACAAAAAAGACT
              A  K  K  T  *                                    203
651  GCTAAGAAGACTTAAAACGTTTATATTCTGCATGCTTTGTGCATTAAGCA
701  TTGCACTGCGGGTAAACTGCACGCTTTCTGATCGCAGTTCATTAAGTAGG
751  ATATGCACAGTGTTTAACCAAGTGTGCAAGTCACTCTGGTCTCAATGTTT
801  TACTGATGTAACCACATGTAAATAACTGTACAAGAAGGAAACAATCACT
851  TTTGTAACGTCTGCTTTGTTATTATTTCTTTTCTACTAGTTAGCTAAAAT
901  AACTGCTTATGGCTTCTTTTAAAATAAAATGATAAAGAAAAAAAAAAAA
951  AAAAAA
```

Figure 11

```
                          :                                                                                                     
Catfish NCAMP-1           : MSAQAEETAPEAAAPVQPSQP---------------AAKKKGPASKAKPASAEKKNKKKKGKGPGKYSCLVINAIQTLGERNG :  68
Danio H1X-like-AAH47192   : ------MPAVVPESAPAPAPAP---------------AEKKAKPAVAASPAKK-----KKKKSKGPGKYSKLVTDAIRLGEKNG :  59
Xenopus H1X-AAH41758      : ----MALELENLHSTEEEDEEEEEGDEMRSRSTRNKGGAASSSGNKKKKK------KNQPGRYSQLVDTIRKLGERNG :  73
Mus H1X-XP 144949         : ----MSVELEALPPTSADG---------------TARKTAKAGGSKAPTQPKRRKN-RKKNQPGKYSQLVETIRKLGERGG :  63
human H1X-BAA11018        : ----MSVELEALPVTAEG---------------MAKKVTKAGGSRALSPSKKRKNSKKRNQPGKYSQLVETIRRLGERNG :  64

Catfish NCAMP-1           : SSLEKLIYNEAKKVNWFDQHGRVYLRYSIRALLQNDTLVQVKG-LGANGSFKLNKKKFIPRTKKSSVKPRKTAKPTKKPAK : 148
Danio H1X-like-AAH47192   : SSLEKLIYNEAKRVSWFDQKNGRMYLRASTRAIVLNDTLVQVKG-LGANGSFKLNKKKLEKKPKK-AASKKATKTEKPTSK : 138
Xenopus H1X-AAH41758      : SSLAKLIYSEAKRVSWFDQQNGRTYLKYSIKALVQNDTLLQVKG-LGANGSFRLNKKKLEGLPYDKKPPPAKPSSSSSNKK : 153
Mus H1X-XP 144949         : SSLARIYAEARKVAWFDQQNGRTYLKYSIRALVQNDTLLQVKG-LGANGSFKLNRKKLEGGAERR-GASAASSPAPKAR-- : 140
human H1X-BAA11018        : SSLAKIIYTEARKVPMFDQQNGRTYIKYSIKALVQNDTLLQVKG-LGANGSFKLNRKKLEGGERRGAPAAATAPATAHKA : 144

Catfish NCAMP-1           : KAAK-----KKKRVSGVKKATPPPEKTSK-PK-----------KADKSPAVSARKASKPKAKQTKKTAKKT- : 203
Danio H1X-like-AAH47192   : KAVT-----KKVSAKKSAKKSPVKKKTPKKT-----SVKKATAKPKKTASKKPKAAAKKKTKSK--- : 192
Xenopus H1X-AAH41758      : QQQ-----GPSSSPSKSHKKAKPKAKAEKEKPKTSSAKAKSPKKSAKG-KRMKGAKPSVRKAPKSAKA : 217
Mus H1X-XP 144949         : ------TAAADRTPARPQ-PERRAHS--------KKAAPAASAKRVKAAAKPSVPKKVPKGRK- : 188
human H1X-BAA11018        : KKRAAPGAAGSRRADKKPARGQKPEQRSHKKGAGAKKDKGGKAKKTAAAGGKRVKAAKPSVPKVPKGRK- : 213
```

FIGURE 16

```
NCAMP-1      PEAAAPVQPSQPAAKKKGPASKAKPASAEKKNKKAKGKGPG

H1-Mus       -----SETAPAEKPAPAKAE-

H1-Human         ---KLNKKAASGEAKPKAKAKSPKKAKA--

H1-Trout     -KAVAAKKSPKKAKKPAT--
```

C-Terminal residues :

```
NCAMP-1
-TAKPTKKPAKKAAKKKKRVSGVKKATPPPEKTSKPKKADKSPAVSAKKASKPKKAKQT
H2A CF   --KGRGKQGGKVRAKAKTRSS--

H2B Trout        -----PDPAKTAPKKGSKKAVTKXA--

H2B Bass1        -----PEPAKSAPKKGSKKAVT-

H2B Bass2        -----PDPAPKTAPKKGSKKAVTKTAG

H1-Trout         -----AEVAPAPAAAAPAKAPKKKA

H1-Trout ---AEVAPAPAAAAPAKAPKKKAAAKPKK-----
```

A

B

SEQUENCE LISTING

<160> NUMBER OF SEQ ID NOS: 32

<210> SEQ ID NO 1
<211> LENGTH: 30
<212> TYPE: PRT

```
<213> ORGANISM: Artificial Sequence
<220> FEATURE:
<223> OTHER INFORMATION: Synthetic Peptide

<400> SEQUENCE: 1

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly
                20                  25                  30

<210> SEQ ID NO 2
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 2

Gly Gly Gly Gly Gly Gly Gly Gly Gly Gly Gly Gly
1               5                   10

<210> SEQ ID NO 3
<211> LENGTH: 203
<212> TYPE: PRT
<213> ORGANISM: Ictalurus punctatus

<400> SEQUENCE: 3

Met Ser Ala Gln Ala Glu Glu Thr Ala Pro Glu Ala Ala Pro Val
1               5                   10                  15

Gln Pro Ser Gln Pro Ala Ala Lys Lys Lys Gly Pro Ala Ser Lys Ala
                20                  25                  30

Lys Pro Ala Ser Ala Glu Lys Lys Asn Lys Lys Lys Gly Lys Gly
            35                  40                  45

Pro Gly Lys Tyr Ser Gln Leu Val Ile Asn Ala Ile Gln Thr Leu Gly
        50                  55                  60

Glu Arg Asn Gly Ser Ser Leu Phe Lys Ile Tyr Asn Glu Ala Lys Lys
65                  70                  75                  80

Val Asn Trp Phe Asp Gln Gln His Gly Arg Val Tyr Leu Arg Tyr Ser
                85                  90                  95

Ile Arg Ala Leu Leu Gln Asn Asp Thr Leu Val Gln Val Lys Gly Leu
            100                 105                 110

Gly Ala Asn Gly Ser Phe Lys Leu Asn Lys Lys Lys Phe Ile Pro Arg
        115                 120                 125

Thr Lys Lys Ser Ser Val Lys Pro Arg Lys Thr Ala Lys Pro Thr Lys
    130                 135                 140

Lys Pro Ala Lys Lys Ala Ala Lys Lys Lys Arg Val Ser Gly Val
145                 150                 155                 160

Lys Lys Ala Thr Pro Pro Glu Lys Thr Ser Lys Pro Lys Lys Ala
                165                 170                 175

Asp Lys Ser Pro Ala Val Ser Ala Lys Lys Ala Ser Lys Pro Lys Lys
            180                 185                 190

Ala Lys Gln Thr Lys Lys Thr Ala Lys Lys Thr
        195                 200

<210> SEQ ID NO 4
<211> LENGTH: 956
<212> TYPE: DNA
<213> ORGANISM: Ictalurus punctatus

<400> SEQUENCE: 4
```

-continued

```
cggcacgagg gttcaatagc atctcaaggc gcttcagaac ttaaagttga accatgtctg    60
ctcaggctga ggaaactgca ccagaagcag cagcaccagt acaaccatca aaccagcgg    120 ccaaaaagaa gggacccgcc agtaaagcaa agcctgcctc tgcagaaaaa aagaacaaaa    180
agaagaaagg gaaagggccc ggaaagtaca gccagctggt gatcaatgct atccaaacgc    240
tgggagagag aaacggctcg tctcttttta agatctacaa cgaggcgaag aaagtgaact    300
ggtttgacca gcagcacggg cgcgtgtacc tccgctactc catccgcgcg ctgctgcaga    360
acgacacgct cgtgcaggtg aagggtctgg gcgccaacgg ctccttcaag ctcaacaaaa    420
agaagttcat ccccagaacc aagaagagct ctgtaaagcc gagaaagact gcgaaaccga    480
ccaaaaagcc agccaaaaaa gcagcgaaga agaagaaaag ggtcagcggc gtgaagaagg    540
cgactccccc cccagagaaa acctccaaac caagaaagc ggataaaagt ccagccgtct    600
ctgccaagaa ggcgagcaag cccaagaaag ctaaacagac aaaaaagact gctaagaaga    660
cttaaaacgt ttatattctg catgctttgt gcattaagca ttgcactgcg gtaaactgc    720 acgctttctg atcgcagttc attaagtagg atatgcacag tgtttaacca agtgtgcaag    780
tcactctggt ctcaatgttt tactgatgta accacatgta ataactgta caaagaagga    840 aacaatcact tttgtaacgt ctgctttgtt attatttctt ttctactagt tagctaaaat    900
aactgcttat ggcttctttt aaataaaat gataaagaa aaaaaaaaa aaaaaa       956
```

```
<210> SEQ ID NO 5
<211> LENGTH: 956
<212> TYPE: DNA
<213> ORGANISM: Ictalurus punctatus
<220> FEATURE:
<221> NAME/KEY: CDS
<222> LOCATION: (54)..(662)
<223> OTHER INFORMATION: ncamp-1 nucleic acid and protein sequence

<400> SEQUENCE: 5
```

```
cggcacgagg gttcaatagc atctcaaggc gcttcagaac ttaaagttga acc atg            56
                                                              Met
                                                              1 tct gct cag gct gag gaa act gca cca gaa gca gca gca cca gta caa         104
Ser Ala Gln Ala Glu Glu Thr Ala Pro Glu Ala Ala Ala Pro Val Gln
         5                  10                  15 cca tca caa cca gcg gcc aaa aag aag gga ccc gcc agt aaa gca aag         152
Pro Ser Gln Pro Ala Ala Lys Lys Lys Gly Pro Ala Ser Lys Ala Lys
    20                   25                  30 cct gcc tct gca gaa aaa aag aac aaa aag aag aaa ggg aaa ggg ccc         200
Pro Ala Ser Ala Glu Lys Lys Asn Lys Lys Lys Gly Lys Gly Pro
 35                  40                  45 gga aag tac agc cag ctg gtg atc aat gct atc caa acg ctg gga gag         248
Gly Lys Tyr Ser Gln Leu Val Ile Asn Ala Ile Gln Thr Leu Gly Glu
50                  55                  60                  65 aga aac ggc tcg tct ctt ttt aag atc tac aac gag gcg aag aaa gtg         296
Arg Asn Gly Ser Ser Leu Phe Lys Ile Tyr Asn Glu Ala Lys Lys Val
                 70                  75                  80 aac tgg ttt gac cag cag cac ggg cgc gtg tac ctc cgc tac tcc atc         344
Asn Trp Phe Asp Gln Gln His Gly Arg Val Tyr Leu Arg Tyr Ser Ile
             85                  90                  95 cgc gcg ctg ctg cag aac gac acg ctc gtg cag gtg aag ggt ctg ggc         392
Arg Ala Leu Leu Gln Asn Asp Thr Leu Val Gln Val Lys Gly Leu Gly
        100                 105                 110 gcc aac ggc tcc ttc aag ctc aac aaa aag aag ttc atc ccc aga acc         440
Ala Asn Gly Ser Phe Lys Leu Asn Lys Lys Lys Phe Ile Pro Arg Thr
    115                 120                 125
```

```
aag aag agc tct gta aag ccg aga aag act gcg aaa ccg acc aaa aag         488
Lys Lys Ser Ser Val Lys Pro Arg Lys Thr Ala Lys Pro Thr Lys Lys
130                 135                 140                 145 cca gcc aaa aaa gca gcg aag aag aag aaa agg gtc agc ggc gtg aag         536
Pro Ala Lys Lys Ala Ala Lys Lys Lys Lys Arg Val Ser Gly Val Lys
                150                 155                 160 aag gcg act ccc ccc cca gag aaa acc tcc aaa ccc aag aaa gcg gat         584
Lys Ala Thr Pro Pro Pro Glu Lys Thr Ser Lys Pro Lys Lys Ala Asp
        165                 170                 175 aaa agt cca gcc gtc tct gcc aag aag gcg agc aag ccc aag aaa gct         632
Lys Ser Pro Ala Val Ser Ala Lys Lys Ala Ser Lys Pro Lys Lys Ala
180                 185                 190 aaa cag aca aaa aag act gct aag aag act taaaacgttt atattctgca           682
Lys Gln Thr Lys Lys Thr Ala Lys Lys Thr
195                 200 tgctttgtgc attaagcatt gcactgcggg taaactgcac gctttctgat cgcagttcat       742
taagtaggat atgcacagtg tttaaccaag tgtgcaagtc actctggtct caatgtttta       802
ctgatgtaac cacatgtaaa taactgtaca aagaaggaaa caatcacttt tgtaacgtct       862
gctttgttat tatttctttt ctactagtta gctaaaataa ctgcttatgg cttcttttaa       922
aataaaatga taaagaaaaa aaaaaaaaaa aaaa                                   956
```

<210> SEQ ID NO 6
<211> LENGTH: 203
<212> TYPE: PRT
<213> ORGANISM: Ictalurus punctatus

<400> SEQUENCE: 6

```
Met Ser Ala Gln Ala Glu Glu Thr Ala Pro Glu Ala Ala Ala Pro Val
1               5                   10                  15

Gln Pro Ser Gln Pro Ala Ala Lys Lys Lys Gly Pro Ala Ser Lys Ala
            20                  25                  30

Lys Pro Ala Ser Ala Glu Lys Lys Asn Lys Lys Lys Gly Lys Gly
        35                  40                  45

Pro Gly Lys Tyr Ser Gln Leu Val Ile Asn Ala Ile Gln Thr Leu Gly
    50                  55                  60

Glu Arg Asn Gly Ser Ser Leu Phe Lys Ile Tyr Asn Glu Ala Lys Lys
65                  70                  75                  80

Val Asn Trp Phe Asp Gln His Gly Arg Val Tyr Leu Arg Tyr Ser
                85                  90                  95

Ile Arg Ala Leu Leu Gln Asn Asp Thr Leu Val Gln Val Lys Gly Leu
            100                 105                 110

Gly Ala Asn Gly Ser Phe Lys Leu Asn Lys Lys Lys Phe Ile Pro Arg
        115                 120                 125

Thr Lys Lys Ser Ser Val Lys Pro Arg Lys Thr Ala Lys Pro Thr Lys
130                 135                 140

Lys Pro Ala Lys Lys Ala Ala Lys Lys Lys Arg Val Ser Gly Val
145                 150                 155                 160

Lys Lys Ala Thr Pro Pro Pro Glu Lys Thr Ser Lys Pro Lys Lys Ala
                165                 170                 175

Asp Lys Ser Pro Ala Val Ser Ala Lys Lys Ala Ser Lys Pro Lys Lys
            180                 185                 190

Ala Lys Gln Thr Lys Lys Thr Ala Lys Lys Thr
        195                 200
```

<210> SEQ ID NO 7
<211> LENGTH: 20

```
<212> TYPE: PRT
<213> ORGANISM: Artificial Sequence
<220> FEATURE:
<223> OTHER INFORMATION: Synthetic Peptide

<400> SEQUENCE: 7

Gly Gly Gly Gly Gly Gly Gly Gly Gly Gly Gly Gly Gly Gly Gly Gly
1               5                   10                  15

Gly Gly Gly Gly
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 8

Thr Cys Gly Thr Cys Gly Thr Thr Gly Thr Cys Gly Thr Thr Gly Thr
1               5                   10                  15

Cys Gly Thr Thr
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 9

Cys Cys Cys Cys Cys Cys Cys Cys Cys Cys Cys Cys Cys Cys Cys Cys
1               5                   10                  15

Cys Cys Cys Cys
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 10

Ala Ala Ala Ala Ala Ala Ala Ala Ala Ala Ala Ala Ala Ala Ala Ala
1               5                   10                  15

Ala Ala Ala Ala
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 11

Thr Thr Thr Thr Thr Thr Thr Thr Thr Thr Thr Thr Thr Thr Thr Thr
1               5                   10                  15

Thr Thr Thr Thr
            20

<210> SEQ ID NO 12
<211> LENGTH: 20
```

```
<212> TYPE: PRT
<213> ORGANISM: Artificial Sequence
<220> FEATURE:
<223> OTHER INFORMATION: Synthetic Peptide

<400> SEQUENCE: 12

Thr Gly Cys Thr Gly Cys Thr Thr Gly Thr Gly Cys Thr Thr Gly Thr
1               5                   10                  15

Gly Cys Thr Thr
            20

<210> SEQ ID NO 13
<211> LENGTH: 192
<212> TYPE: PRT
<213> ORGANISM: Danio rerio

<400> SEQUENCE: 13

Met Pro Ala Val Val Glu Ser Ala Pro Ala Pro Ala Pro Ala Pro
1               5                   10                  15

Ala Glu Lys Lys Ala Lys Pro Ala Val Ala Ala Ser Pro Ala Lys Lys
                20                  25                  30

Lys Lys Lys Lys Ser Lys Gly Pro Gly Lys Tyr Ser Lys Leu Val Thr
            35                  40                  45

Asp Ala Ile Arg Thr Leu Gly Glu Lys Asn Gly Ser Ser Leu Phe Lys
        50                  55                  60

Ile Tyr Asn Glu Ala Lys Lys Val Ser Trp Phe Asp Gln Lys Asn Gly
65                  70                  75                  80

Arg Met Tyr Leu Arg Ala Ser Ile Arg Ala Leu Val Leu Asn Asp Thr
                85                  90                  95

Leu Val Gln Val Lys Gly Phe Gly Ala Asn Gly Ser Phe Lys Leu Asn
            100                 105                 110

Lys Lys Lys Leu Glu Lys Lys Pro Lys Lys Ala Ala Ser Lys Lys Ala
        115                 120                 125

Thr Lys Lys Thr Glu Lys Pro Thr Ser Lys Lys Ala Val Thr Lys Lys
    130                 135                 140

Val Ser Ala Lys Lys Ser Ala Lys Lys Ser Pro Val Lys Lys Lys Thr
145                 150                 155                 160

Pro Lys Lys Thr Ser Val Lys Lys Ala Thr Ala Lys Pro Lys Lys Thr
                165                 170                 175

Ala Ser Lys Lys Pro Lys Ala Ala Lys Lys Lys Thr Lys Ser Lys
            180                 185                 190

<210> SEQ ID NO 14
<211> LENGTH: 217
<212> TYPE: PRT
<213> ORGANISM: Xenopus laevis

<400> SEQUENCE: 14

Met Ala Leu Glu Leu Glu Glu Asn Leu His Ser Thr Glu Glu Glu Asp
1               5                   10                  15

Glu Glu Glu Glu Glu Glu Glu Gly Asp Glu Met Arg Ser Arg Ser Thr
                20                  25                  30

Arg Asn Lys Gly Gly Ala Ala Ser Ser Gly Asn Lys Lys Lys Lys
            35                  40                  45

Lys Lys Lys Asn Gln Pro Gly Arg Tyr Ser Gln Leu Val Val Asp Thr
        50                  55                  60

Ile Arg Lys Leu Gly Glu Arg Asn Gly Ser Ser Leu Ala Lys Ile Tyr
65                  70                  75                  80
```

```
Ser Glu Ala Lys Lys Val Ser Trp Phe Asp Gln Gln Asn Gly Arg Thr
            85                  90                  95

Tyr Leu Lys Tyr Ser Ile Lys Ala Leu Val Gln Asn Asp Thr Leu Leu
            100                 105                 110

Gln Val Lys Gly Val Gly Ala Asn Gly Ser Phe Arg Leu Asn Lys Lys
            115                 120                 125

Lys Leu Glu Gly Leu Pro Tyr Asp Lys Pro Pro Ala Lys Pro
            130                 135                 140

Ser Ser Ser Ser Ser Asn Lys Lys Gln Gln Gln Gly Pro Ser Ser
145                 150                 155                 160

Ser Pro Ser Lys Ser His Lys Lys Ala Lys Pro Lys Ala Lys Ala Glu
            165                 170                 175

Lys Glu Lys Pro Lys Thr Ser Ser Ala Lys Ala Lys Ser Pro Lys Lys
            180                 185                 190

Ser Ala Ala Lys Gly Lys Lys Met Lys Lys Gly Ala Lys Pro Ser Val
            195                 200                 205

Arg Lys Ala Pro Lys Ser Lys Ala
            210                 215

<210> SEQ ID NO 15
<211> LENGTH: 188
<212> TYPE: PRT
<213> ORGANISM: Mus musculus

<400> SEQUENCE: 15

Met Ser Val Glu Leu Glu Glu Ala Leu Pro Pro Thr Ser Ala Asp Gly
1               5                   10                  15

Thr Ala Arg Lys Thr Ala Lys Ala Gly Gly Ser Ala Ala Pro Thr Gln
            20                  25                  30

Pro Lys Arg Arg Lys Asn Arg Lys Asn Gln Pro Gly Lys Tyr Ser
            35                  40                  45

Gln Leu Val Val Glu Thr Ile Arg Lys Leu Gly Glu Arg Gly Gly Ser
        50                  55                  60

Ser Leu Ala Arg Ile Tyr Ala Glu Ala Arg Lys Val Ala Trp Phe Asp
65                  70                  75                  80

Gln Gln Asn Gly Arg Thr Tyr Leu Lys Tyr Ser Ile Arg Ala Leu Val
            85                  90                  95

Gln Asn Asp Thr Leu Leu Gln Val Lys Gly Thr Gly Ala Asn Gly Ser
            100                 105                 110

Phe Lys Leu Asn Arg Lys Lys Leu Glu Gly Gly Ala Glu Arg Arg Gly
            115                 120                 125

Ala Ser Ala Ala Ser Ser Pro Ala Pro Lys Ala Arg Thr Ala Ala Ala
        130                 135                 140

Asp Arg Thr Pro Ala Arg Pro Gln Pro Glu Arg Arg Ala His Lys Ser
145                 150                 155                 160

Lys Lys Ala Ala Ala Ala Ala Ser Ala Lys Lys Val Lys Lys Ala Ala
            165                 170                 175

Lys Pro Ser Val Pro Lys Val Pro Lys Gly Arg Lys
            180                 185

<210> SEQ ID NO 16
<211> LENGTH: 213
<212> TYPE: PRT
<213> ORGANISM: Homo sapiens

<400> SEQUENCE: 16

Met Ser Val Glu Leu Glu Glu Ala Leu Pro Val Thr Thr Ala Glu Gly
```

```
                1               5                   10                  15
Met Ala Lys Lys Val Thr Lys Ala Gly Gly Ser Ala Ala Leu Ser Pro
                20                  25                  30

Ser Lys Lys Arg Lys Asn Ser Lys Lys Asn Gln Pro Gly Lys Tyr
        35                  40                  45

Ser Gln Leu Val Val Glu Thr Ile Arg Arg Leu Gly Glu Arg Asn Gly
    50                  55                  60

Ser Ser Leu Ala Lys Ile Tyr Thr Glu Ala Lys Lys Val Pro Trp Phe
65                  70                  75                  80

Asp Gln Gln Asn Gly Arg Thr Tyr Leu Lys Tyr Ser Ile Lys Ala Leu
                85                  90                  95

Val Gln Asn Asp Thr Leu Leu Gln Val Lys Gly Thr Gly Ala Asn Gly
            100                 105                 110

Ser Phe Lys Leu Asn Arg Lys Lys Leu Glu Gly Gly Glu Arg Arg
            115                 120                 125

Gly Ala Pro Ala Ala Thr Ala Pro Ala Pro Thr Ala His Lys Ala
        130                 135                 140

Lys Lys Ala Ala Pro Gly Ala Ala Gly Ser Arg Arg Ala Asp Lys Lys
145                 150                 155                 160

Pro Ala Arg Gly Gln Lys Pro Glu Gln Arg Ser His Lys Lys Gly Ala
                165                 170                 175

Gly Ala Lys Lys Asp Lys Gly Gly Lys Ala Lys Lys Thr Ala Ala Ala
                180                 185                 190

Gly Gly Lys Lys Val Lys Lys Ala Ala Lys Pro Ser Val Pro Lys Val
            195                 200                 205

Pro Lys Gly Arg Lys
        210

<210> SEQ ID NO 17
<211> LENGTH: 15
<212> TYPE: PRT
<213> ORGANISM: Mus musculus

<400> SEQUENCE: 17

Ser Glu Thr Ala Pro Ala Glu Lys Pro Ala Pro Ala Lys Ala Glu
1               5                   10                  15

<210> SEQ ID NO 18
<211> LENGTH: 25
<212> TYPE: PRT
<213> ORGANISM: Homo sapiens

<400> SEQUENCE: 18

Lys Leu Asn Lys Lys Ala Ala Ser Gly Glu Ala Lys Pro Lys Ala Lys
1               5                   10                  15

Ala Lys Ser Pro Lys Lys Ala Lys Ala
            20                  25

<210> SEQ ID NO 19
<211> LENGTH: 17
<212> TYPE: PRT
<213> ORGANISM: Oncorhynchus mykiss

<400> SEQUENCE: 19

Lys Ala Val Ala Ala Lys Lys Ser Pro Lys Lys Ala Lys Lys Pro Ala
1               5                   10                  15

Thr
```

```
<210> SEQ ID NO 20
<211> LENGTH: 19
<212> TYPE: PRT
<213> ORGANISM: Ictalurus punctatus

<400> SEQUENCE: 20

Lys Gly Arg Gly Lys Gln Gly Gly Lys Val Arg Ala Lys Ala Lys Thr
1               5                   10                  15

Arg Ser Ser

<210> SEQ ID NO 21
<211> LENGTH: 20
<212> TYPE: PRT
<213> ORGANISM: Oncorhynchus mykiss
<220> FEATURE:
<221> NAME/KEY: misc_feature
<222> LOCATION: (19)..(19)
<223> OTHER INFORMATION: Xaa can be any naturally occurring amino acid

<400> SEQUENCE: 21

Pro Asp Pro Ala Lys Thr Ala Pro Lys Lys Gly Ser Lys Lys Ala Val
1               5                   10                  15

Thr Lys Xaa Ala
            20

<210> SEQ ID NO 22
<211> LENGTH: 17
<212> TYPE: PRT
<213> ORGANISM: Centropristis striata

<400> SEQUENCE: 22

Pro Glu Pro Ala Lys Ser Ala Pro Lys Lys Gly Ser Lys Lys Ala Val
1               5                   10                  15

Thr

<210> SEQ ID NO 23
<211> LENGTH: 22
<212> TYPE: PRT
<213> ORGANISM: Cynoscion regalis

<400> SEQUENCE: 23

Pro Asp Pro Ala Pro Lys Thr Ala Pro Lys Lys Gly Ser Lys Lys Ala
1               5                   10                  15

Val Thr Lys Thr Ala Gly
            20

<210> SEQ ID NO 24
<211> LENGTH: 26
<212> TYPE: PRT
<213> ORGANISM: Oncorhynchus mykiss

<400> SEQUENCE: 24

Ala Glu Val Ala Pro Ala Pro Ala Ala Ala Pro Ala Lys Ala Pro
1               5                   10                  15

Lys Lys Lys Ala Ala Ala Lys Pro Lys Lys
            20                  25

<210> SEQ ID NO 25
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 25
```

Ala Lys Lys Ala
1

<210> SEQ ID NO 26
<211> LENGTH: 11
<212> TYPE: PRT
<213> ORGANISM: Ictalurus punctatus

<400> SEQUENCE: 26

Gly Ala Ser Gly Ser Phe Lys Leu Asn Lys Lys
1               5                   10

<210> SEQ ID NO 27
<211> LENGTH: 21
<212> TYPE: PRT
<213> ORGANISM: Lacobacillus plantarum

<400> SEQUENCE: 27

Ala Tyr Ser Leu Gln Met Gly Ala Thr Ala Ile Lys Gln Val Lys Lys
1               5                   10                  15

Leu Phe Lys Lys Trp
            20

<210> SEQ ID NO 28
<211> LENGTH: 28
<212> TYPE: PRT
<213> ORGANISM: Hyalophora cecropia

<400> SEQUENCE: 28

Pro Lys Trp Lys Leu Phe Lys Lys Ile Glu Lys Val Gly Gln Asn Ile
1               5                   10                  15

Arg Asp Gly Ile Ile Lys Ala Gly Pro Ala Val Ala
            20                  25

<210> SEQ ID NO 29
<211> LENGTH: 22
<212> TYPE: PRT
<213> ORGANISM: Acanthoscurria gomesiana

<400> SEQUENCE: 29

Phe Lys Phe Leu Ala Lys Lys Val Ala Lys Thr Val Ala Lys Gln Ala
1               5                   10                  15

Ala Lys Gln Gly Ala Lys
            20

<210> SEQ ID NO 30
<211> LENGTH: 22
<212> TYPE: PRT
<213> ORGANISM: Bufo gargarizans

<400> SEQUENCE: 30

Ala Gly Arg Gly Lys Gln Gly Gly Lys Val Arg Ala Lys Ala Lys Thr
1               5                   10                  15

Arg Ser Ser Arg Ala Gly
            20

<210> SEQ ID NO 31
<211> LENGTH: 23
<212> TYPE: PRT
<213> ORGANISM: Xenopus laevis

<400> SEQUENCE: 31

Gly Ile Gly Lys Phe Leu His Ser Ala Lys Lys Phe Gly Lys Ala Phe

```
Val Gly Glu Ile Met Asn Ser
                20

<210> SEQ ID NO 32
<211> LENGTH: 30
<212> TYPE: PRT
<213> ORGANISM: Homo sapiens
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid

<400> SEQUENCE: 32

Lys Ala Pro Arg Lys Gln Leu Ala Thr Pro Glu Pro Ala Lys Ser Ala
1               5                  10                  15

Pro Ala Pro Lys Lys Gly Xaa Lys Lys Xaa Val Thr Lys Ala
            20                  25                  30
```

TELEOST DERIVED ANTIMICROBIAL POLYPEPTIDES

PRIORITY CLAIM

This application claims priority under 35 U.S.C. §119(e) to provisional application No. 60/545,370, filed Feb. 18, 2004 and 60/623,909, filed Nov. 1, 2004, the contents of which are incorporated herein by reference.

FIELD OF THE INVENTION

The invention is directed to an isolated polypeptide which (a) is obtainable from a teleost; (b) has antimicrobial activity; (c) binds to oligoguanosine and/or CpG (SEQ ID NO:7); (d) comprises 58 strongly basic amino acids selected from the group consisting of K and R; (e) comprises 50 hydrophobic amino acids selected from the group consisting of A, I, L, F, W and V; (f) comprises 50 polar amino acids selected from the group consisting of N, C, Q, S, T and Y and (g) contains 11 lysine-rich motifs and antimicrobial fragments thereof as well as methods for preparing said polypeptides, compositions and libraries comprising said polypeptide(s) and uses of said polypeptide(s), particularly in treating microbial infections. The invention is further directed to a nucleic acid(s) encoding said polypeptide, microarrays comprising said nucleic acid(s) and uses for said nucleic acid(s). Furthermore, the invention is directed to an antibody which binds to the polypeptide of the present invention and uses for said antibodies.

BACKGROUND OF THE INVENTION

Bacterial DNA initiates inflammatory responses and is responsible for development of some level of innate immunity in mammals (Ashkar et al., 2002, Curr. Mol. Med. 2: 545-556; Pisetsky, 1999, Immunol. Res. 19: 35-46; Krieg et al., 1995, Nature 374: 546-549; Krieg, 1999, J. Gene Med. 1: 56-63). The oligodeoxynucleotide (ODN) ligand specificities of mammalian NK cells, antigen presenting cells (B-cells, macrophages, dendritic cells) and T-cells have been extensively reviewed (Krieg, 2000, Curr. Opin. Immunol. 12:35-43; Krieg, 1999, Biochim. Biophys. Acta 1489:107-116; Pisetsky et al., 1999, Biochem. Pharmacol. 58:1981-1988; Pisetsky, 1996, Immunity 5:303-310; Pisetsky et al., 1993, Mol. Biol. Rep. 18:217-221; Krieg, 2000, Vaccine 9:618-222; Scheule, 2000, Adv. Drug Deliv. Rev. 44:119-134, Weiner, 2000, J. Leukoc. Biol. 68:455-463, Lipford et al., 1998, Trends Microbiol. 6:496-500).

The chemistry and conformation of single base phosphodiester (Po) oligodeoxyguanosine was unique compared to other single base oligos. Po (dG30 (only) (SEQ ID NO:1) and Ps single base ODNs were mitogenic for B-cells (Pisetsky et al., 1993, Mol Biol Rep. 18:217-221). Interestingly, negative immunoregulatory activities were also reported for single base ODNs as well as for CpG (SEQ ID NO:7) ODNs. Pretreatment of J774 cells with Po dG30 (SEQ ID NO:1) inhibited E. coli DNA, LPS and CpG (SEQ ID NO:7) activation of IL-12 (Pisetsky et al., 1993, Mol. Biol. Rep. 18:217-221) and nitric oxide (Zhu et al., 2002, J. Leukoc. Biol. 71:686-694) production. All other Po single base ODNs (i.e. dA, dT, dC) tested did not produce this effect. It appears that single base ODNs may have different effects based on whether they are Ps or Po and on the target cell type involved in the immune response (Zhu et al., 2002, J. Leukoc. Biol. 72:1154-1163).

Other studies of the effects of unique nucleic acids on immune function have been published. Conjugation of dG "Runs" to CpG (SEQ ID NO:7) (i.e. dG6 (SEQ ID NO:6) produced an ODN that bound mouse APC (Lee et al., 2000, J Immunol 165:3631-3639), and CD8 positive T-cells (Lipford et al., 2000, Immunology 101:46-52). In these studies, binding was followed by activation as shown by secretion of TNF-alpha and IL-12 (Lipford et al., 2000, Immunology 101:46-52) as well as initiation of T-cell proliferation and cytotoxicity (Lee et al., 2000, J Immunol 165:3631-3639). Conjugation of dG "Runs" to 3' and 5' ends of CpG ODN (SEQ ID NO:7) enhanced NK cell lytic activity (Ballas et al., 1996, J. Immunol. 157:1840-1845). Costimulatory effects of guanosine-rich (G-rich) ODNs were shown in T-cells where costimulation by G-rich ODNs induced CTL activity (Lipford et al., 1998, Trends Microbiol. 6:496-500). CpG (SEQ ID NO:7) palindromes containing flanking sequences or "runs" of 12 guanosine nucleotides (i.e. dG12 (SEQ ID NO:2) bind to and activate mouse NK cells (Kimura et al., 1994, J. Biochem. 116:991-994).

There are several different classes/types of DNA binding proteins on mammalian cells represented by a limited number of germ-line encoded receptors that are expressed predominantly on antigen presenting cells (with low levels of expression on T-cells and NK cells). These proteins are referred to as pattern recognition receptors (PRR) (Krug et al., 2003, J. Immunol. 170: 3468-3477; Sano et al., 2003, J. Immunol. 170: 2367-2373) and they bind to pathogen associated molecular pattern ligands (PAMP) of microbial origin. The PAMPS include LPS, peptidoglycan, certain lipoproteins, CpG oligodeoxynucleotides (ODNs) (SEQ ID NO:7), etc. The most widely distributed of the PRR that bind ODNs are the Toll-like receptor 9, Mac-1 (CD 11b/CD18) (Stacey et al., 2000, Curr. Top. Microbiol. Immunol. 247: 41-58; Takeda et al., 2003, Ann. Rev. Immunol. 21: 335-376; Hemmi et al., 2000, Nature, 408: 740-745, Benimetskaya, 1997, Nat. Med. 3: 414420; Bauer et al., 2001, J. Immunol. 166: 5000-5007) and Scavenger receptor-A (Kimura et al., 1994, J. Biochem. (Tokyo) 116:991-994; Peiser et al., 2002, Curr. Opin. Immunol. 14:123-128). ODN binding to PRR may cause either activation or inhibitory responses depending on the ODN concentration and target cell type. In addition, ligation of PRR in vivo by ODNs may also produce different pathways of immunoregulation such as autoimmunity, Th1 bias activation, etc. (Bauer et al., 2001, Proc. Natl. Acad. Sci. U S A. 98: 9237-9242; Chuang et al., 2002, J. Leuk. Biol. 71: 538-544; Kerkmann et al., 2003, J. Immunol. 170: 4465-4474).

Antimicrobial Proteins and Peptides

Naturally occurring antimicrobial proteins and peptides (AMP) have been identified from plant, invertebrate and vertebrate species (Hancock et al., 2000, Trend Microbiol., 8:402-410; Hancock et al., 1995, 37:135-275; Hanson et al., 2000, In: Cytotoxic Cells: Basic Mechanisms and Medical Application, M V Sitkovsky and P A Henkart (eds), Lippincott Williams and Wilkins, Phil, Pa. 213-227; Vizioli et al., 2000, Trends Pharmacol. Sci., 23: 494-496; Zhai et al., 2000, Biochim. Biophys. Acta 1469: 87-99). These AMPs have been classified based on both chemical and conformational properties and they can be differentiated based on whether the active form is a peptide (i.e. 17-35 aa in length) or a protein (>50 aa). An additional distinguishing property of AMP is their cationic nature with little to no amino acid sequence identity across all the members of this very large group. For example, cecropins, magainins and defensins from silk moth, Xenopus and mammals (respectively) are all low mw AMP. Although they share lysine rich regions and are inducible, they have no sequence homology. The functional characteristic of this large group of AMP is based on their common ability to kill bacteria and (in some cases) eukaryotic cells.

The amino acid content of these AMPs provides clues regarding the common chemical and physical features that may be responsible for their bactericidal effects. An example is the recently described AMP Cupiennin-1 (Kulm-Nentwig et al., 2002, J. Biol. Chem., 13: 11208-11216). This 35 aa basic peptide has 8 lysine residues, is present in the venom of *Cupiennius salei* (a hunting spider found in Central America), is amphipathic and has bactericidal activities against Gram negative and Gram positive bacteria. This peptide may be similar to other AMPs (e.g. magainins; Jacob et al., 1994, Ciba Foundation Symposium 186:197-216) regarding the mechanism of binding to bacterial cells. It was predicted to fold into an amphipathic alpha-helix when it inserts into the bacterial cell membrane. Differential sensitivities of eukaryotic versus prokaryotic cells are thought to be based on the low cholesterol content and relatively high negative charge density of bacterial cell walls compared to eukaryotic cells (Jacob et al., 1994, Ciba Foundation Symposium 186: 197-216).

Another type of AMP is not naturally occurring, but is generated in vitro by proteolytic digestion or acid hydrolysis of some precursor, larger mw molecule. These AMP are relevant innate immune response effector substances. One interesting class that has been studied is histone like proteins. The traditional cellular location of histone proteins (H1) is in the nucleus associated with chromatin fibers either in the form of linker histone 1 or core histones (H2a, H2b, H3 and H4) that form nucleosomes. However, studies performed in higher vertebrates have shown that many cells of the immune system express cytoplasmic and membrane forms of these proteins (Ojcius et al., 1991, Immunol. Lett., 28: 101-108; Watson et al., 1994, Biochem. Soc. Trans. 22:199S; Watson et al., 1995, Biochem. Pharmacol., 50: 299-309; Holers et al., 1985, J. Clin. Invest. 76: 991-998; Bennett et al., 1985, J. Clin. Invest. 76: 2182-2190; Emlen et al., 1992, J. Immunol. 148: 3042-3048; Watson et al., 1995, Biochem. Pharm. 50: 299-309; Bolton et al., 1997, J. Neurocytology 26: 823-831; Bennet et al., 1988, J. Immunol. 140: 2937-2942; Rose et al., 1998, Inf. Immun. 66: 3255-3263; Eggena et al., 2000. J. Autoimm. 14: 83-97; Kubota et al., 1990, Immunol. Lett. 23:187-193). The function(s) of histone like membrane proteins (HLMP) cationic proteins have generally not been ascribed to ligand or receptor activities except for thyroglobulin binding by an H1 receptor on mouse macrophages (Brix et al., 1998, Clin. Invest. 102: 283-293) and DNA binding by a 28 kDa protein on "normal" human lymphocytes (Gasparro et al., 1990, Photochem. Photobiol., 52: 315-321). Evidence for the association of cell-derived. and/or cell membrane histone H1 as a participant in antibacterial innate immunity has also been provided by studies of human ileal mucosal extracts (Rose et al., 1998, Inf. Immun. 66: 3255-3263) and human ulcerative colitis (UC) (Eggena et al., 2000. J. Autoimm. 14: 83-97). In both cases H1 was either released from villus epithelial cells (Rose et al., 1998, Inf. Immun. 66: 3255-3263) or was associated with a serum marker for UC (Eggena et al., 2000, J. Autoimm. 14: 83-97). In addition, Raji cells express 14, 17, 18, 33 and 34 kDa DNA binding proteins (Kubota et al., 1990, Immunol. Lett. 23: 187-193). These histone or histone-like proteins were described as being responsible for the binding, endocytosis and degradation of exogenous DNA. Interestingly, the thyroglobulin receptor on the cell surface of J774 (mouse) macrophages is an H1 protein (Brix et al., 1998, J. Clin. Invest. 102: 283-293).

Teleost Derived Immune Activity

Histone proteins and peptides with antimicrobial activities have been isolated from various teleosts, e.g., salmon blood, liver, intestine and mucus (Patrzykat et al., 2001, Antimicrob. Agents Chemother, 45:1337-1342). Catfish skin, epithelial cells and mucus contain H2A-like (Parasin-I) and H2B-like molecules (Cho et al., 2002, FASEB J. 16: 429-431). Histone release from teleost cells require tissue injury; thus, membrane expression of histone-like proteins was not determined. CpG (SEQ ID NO:7)-induced activation of rainbow trout macrophages was determined by induction of IL-1β and IFN-like cytokines (Jorgensen et al., 2001, Fish Shellfish Immunol., 8: 673-682). Similarly, CpG (SEQ ID NO:7) activated leukocytes from Atlantic salmon had increased interferon production (Jorgensen et al., 2001, Dev. Comp. Immunol., 4: 313-321).

Nonspecific cytotoxic cells from catfish have been found to be activitated by bacterial DNA and ODN's (Oumouna et al., 2002, Dev. Comp. Immunol. 26:257-269). Cellular activation resulted from the binding of synthetic ODNs (sODN) to NK-like nonspecific cytotoxic cells (NCC). Differences were described in the teleost cells compared to mammalian "canonical" dogma. The preferred binding motifs for mammalian cells consist of -GACGTT- (mice) and -GTCGTT- (humans) (Krieg A M., 2002, Curr. Opin. Immunol. 12:35-43) and GpC dinucleotides do not bind these cells. The optimum immunostimulatory motif for teleosts was composed of either 5'-C/AT/AGCTT-3' or 5'-GTCGTT-3' (Oumouna et al., 2002, Dev Comp Immunol 26:257-269). Methylation of cytosine inhibited teleost activation responses to sODNs. NCCs were activated by sODNs containing dinucleotides flanked by consecutive deoxyguanosine residues (dG runs) in addition to the single base oligodeoxyguanosine 20-mer nucleotide (i.e. dG20 (SEQ ID NO:6)) (Oumouna et al., 2002, Dev. Comp. Immunol. 26:257-269).

Studies have been conducted to determine if SR-A-Type-I was responsible for dG20 (SEQ ID NO:6) binding activity to NCC (Kaur et al., 2003, Fish Shellfish Immunol. 15:169-181). Those results demonstrated that total binding by dG20 (SEQ ID NO:6) to NCC could not be explained solely by expression of Scavenger Receptor-A (SR-A) because antibody to SR-A or SR-A ligands (i.e. dextran sulfate, polyvinyl sulfate) could only compete 40-50% of total dG20 (SEQ ID NO:6) binding. However, antimicrobial proteins have been isolated from Atlantic salmon (*Salmo salar*) (Richards et al., 2001, Biochem. Biophys. Res. Comm. 284: 549-555; from striped bass (Noga et al., 2001, Parasitol. 123: 57-65; U.S. Pat. No. 6,753,407); Coho salmon and flounder (Patizkat et al., 2001, Antimicrob. Agents Chemother. 45: 1337-1342); rainbow trout (Fernandez et al., 2002. Biochem. J. 368: 611-620); from catfish (Park et al., 1998, FEBS Lett. 437: 258-262; U.S. Pat. No. 6,316,594; Cho et al., 2002, FASEB J. 16: 429-431); from tiger shrimp (*Peaeus monodon*) (U.S. Pat. Appl. Pub. No. 2004/0235738) for model studies of the role of histone-like proteins in antimicrobial immunity).

Toll-like receptor proteins have not yet been identified on teleost cells although a trout homologue has been obtained from an EST library of differentially expressed liver genes (Bayne et al., 2001, Dev. Comp. Immunol. 25: 205-17). However, its function remains unknown. Similarly, two additional EST's from zebrafish (Accession numbers: BF158452 and BG304206) have identified fragments of Toll-like genes, but their functions also remain unknown. Complete sequencing and functional characterization of these molecules and other PRR will provide invaluable insight into the evolution of these receptors and their role in pathogen resistance.

SUMMARY OF THE INVENTION

The invention is directed to a novel isolated polypeptide(s) which (a) is obtainable from a teleost, mammalian macrophages or mammalian monocytes; (b) has antimicrobial activity; (c) binds to oligoguanosine; (d) comprises 58 strongly basic amino acids selected from the group consisting of K and R; (e) comprises 50 hydrophobic amino acids selected from the group consisting of A, I, L, F, W and V; (f) comprises 50 polar amino acids selected from the group consisting of N, C, Q, S, T and Y and (g) contains 11 lysine-rich motifs and antimicrobial fragments thereof as well as methods for preparing said polypeptides, compositions comprising said polypeptide(s) and uses of said polypeptide(s). In a specific embodiment, the polypeptide of the present invention has a molecular weight of about 22 kD to about 30 kD. In yet another specific embodiment, the polypeptide of the present invention may be obtainable from an *Ictalurus* sp., particularly, *Ictalurus punzctatus*.

In a more specific embodiment, the polypeptide(s) of the present invention comprises amino acid sequences selected from the group consisting of

```
(amino acid residues 1-60 of SEQ ID NO: 3);
MSAQAEETAPEAAAPVQPSQPAAKKKGPASKAKPASAEKKNKKKKGKGPG

KYSQLVINAI;

(amino acid residues 1-118 of SEQ ID NO: 3);
MSAQAEETAPEAAAPVQPSQPAAKKKGPASKAKPASAEKKNKKKKGKGPG

KYSQLVINAIQTLGERNGSSLFKIYNEAKKVNWFDQQHGRVYLRYSIRAL

LQNDTLVQVKGLGANGSF (amino acid residues 27-51 of SEQ ID NO: 3);
GPASKAKPASAEKKNKKKKGKGPGKY (amino acid residues 136-159 of SEQ ID NO: 3)
PRKTAKPTKKPAKKAAKKKKRVSG
and (amino acid residues 173-203 of SEQ ID NO: 3)
PKKADKSPAVSAKKASKPKKAKQTKKTAKKT
```

The polypeptide of the present invention may be selected from the group consisting of:
 (a) A polypeptide depicted in SEQ ID NO:3;
 (b) A polypeptide that is an allelic variant of SEQ ID NO:3;
 (c) an amino acid sequence is encoded by a nucleic acid molecule that hybridizes under stringent conditions to the opposite strand of a nucleic acid molecule shown in SEQ ID NO:4;
 (d) a polypeptide depicted in SEQ ID NO:3 with conservative amino acid substitutions and
 (e) a fragment of (a)-(d), wherein said fragment comprises at least 24 contiguous amino acids.

The invention is also directed to compositions, libraries and kits comprising said polypeptides of the present invention. The compositions of the present invention may comprise the polypeptide of the present invention and an excipient or carrier. The compositions may further comprise another antimicrobial compound.

The polypeptides and compositions comprising said polypeptides have a number of uses. In particular, the invention is directed to the use of the polypeptide of the present invention for the manufacture of a medicament for treatment of a disorder resulting from a microbial infection. Further the invention is directed to a pharmaceutical composition comprising said polypeptide for use in treating a disorder resulting from a microbial infection. In a related aspect, the invention is directed to a method for inhibiting microbial growth in a subject in need thereof comprising administering to said subject the polypeptide or composition of the present invention in an amount effective to inhibit microbial growth, including but not limited to bacterial, protozoa, including parasitic protozoa or fungal growth, in said subject. The subject may be a fish or a mammal, more specifically which may be a human subject. In another related aspect, the invention is directed to a method for inhibiting microbial growth in a subject in need thereof comprising administering to said subject the polypeptide or composition of the present invention in an amount effective to inhibit microbial growth in said subject. The method of the present invention may further comprise administering either simultaneously or sequentially another antimicrobial compound. The polypeptide or composition of the present invention may be used to reduce resistance of antibiotic resistant bacteria in a subject comprising administering to said subject an amount of the polypeptide or composition of the present invention effective to reduce antibiotic resistance.

The polypeptides of the present invention are further directed to a method for identifying other antimicrobial compounds. Specifically, the invention is directed to a method of identifying an antimicrobial polypeptide comprising contacting candidate compounds with the polypeptide or library of the present invention and selecting those compounds capable of inhibiting the bioactivity of said polypeptide.

The invention is further directed to an isolated nucleic acid, said nucleic acid having a nucleotide sequence at least 95% identical to a sequence selected from the group consisting of:
 (a) a nucleic acid encoding an antimicrobial polypeptide depicted in SEQ ID NO:3;
 (b) a nucleic acid consisting of SEQ ID NO:4 which encodes an antimicrobial polypeptide depicted in SEQ ID NO:3
 (c) a nucleic acid which is an allelic variant of SEQ ID NO:4;
 (d) a nucleic acid which hybridizes under stringent conditions to any one of the nucleic acid specified in (a)-(c);
 (e) a nucleic acid that is a complement of the nucleic acid specified in (a)-(d) and
 (f) a nucleic acid fragment of (a)-(e) containing at least 70 nucleotides.

The invention also is directed to constructs, vectors and host cells comprising said nucleic acid. The nucleic acid may be a DNA or RNA sequence. The DNA sequence may be a genomic DNA or cDNA. The invention is further directed to compositions, kits and/or microarrays comprising said nucleic acids. The kits may comprise one or more nucleic acids of the present invention or other nucleic acids. Furthermore, the kits may comprise detectable labels or reagents. Furthermore, the kits of the present invention may further comprise microarrays.

The nucleic acids of the present invention may also be used to inhibit medical disorders resulting from a microbial infection. Thus the invention is directed to the use of the nucleic acid of the present invention for the manufacture of a medicament for use in treating a medical disorder resulting from a microbial infection. As with polypeptides, the invention is directed to a pharmaceutical composition comprising said nucleic acid for use in treating a disorder resulting from a microbial infection. In a related aspect, the invention is directed to a method for inhibiting microbial growth in a subject in need thereof comprising administering to said subject the nucleic acid or composition of the present invention in an amount effective to inhibit microbial growth, including but not limited to bacterial, protozoa, parasitic or fungal growth, in said subject.

The invention is further directed to nucleic acid probes or primers which are fragments of the nucleic acids of the present invention. In a specific embodiment, said probes or primers are at least 70 nucleotides in length, more preferably at least 180 nucleotide units in length.

The nucleic acids, either full length or fragments thereof may be used to detect antimicrobial compounds in a biological sample. Specifically, the invention is directed to a method for detecting the presence or absence of an antimicrobial polypeptide in a sample comprising (a) determining the presence or absence of a nucleic acid hybridizing to the nucleic acid (full length or fragment thereof) or microarray of the present invention and (b) assaying said sample for antimicrobial activity.

The invention is further directed to an antibody which binds the polypeptide of the present invention. The antibody may be a polyclonal or monoclonal antibody. In a related aspect, the invention is directed to a library comprising at least one antibody of the present invention. The invention is further directed to a kit comprising one or more antibodies of the present invention or a library of antibodies, where at least one of the antibodies is an antibody of the present invention.

In specific embodiments, the kit may comprise (a) the antibody of the present invention attached to a solid support and (b) the antibody of the present invention comprising a detectable label. In another specific embodiment, the invention is directed to the antibody of the present invention and a binding partner for said antibody, wherein said binding partner is conjugated to a detectable label.

The invention further relates to using said antibody to identify an antimicrobial compound comprising contacting candidate compounds with the antibody(ies), library of antibodies of the present invention and selecting those compounds capable of binding said antibody.

The invention further relates to a method for preparing an antibody which binds the polypeptide of the present invention comprising (a) optionally conjugating said polypeptide to a carrier protein;

(b) immunizing a host animal with said polypeptide or polypeptide-carrier protein conjugate of step (c) with an adjuvant and (c) obtaining antibody from said immunized host animal. In a specific embodiment, the antibody is a monoclonal antibody. The invention is also directed to a method for obtaining said monoclonal antibody comprising (a) immunizing an animal with said polypeptide;

(b) isolating antibody producing cells from the animal;

(c) fusing the antibody producing cells with immortalized cells in culture to form monoclonal antibody-producing hybridoma cells;

(d) culturing the hybridoma cells; and (e) isolating from the culture monoclonal antibodies which bind to said polypeptide.

The invention is further directed to hybridoma cells producing said monoclonal antibodies of the present invention.

The invention is additionally directed to methods for obtaining the polypeptide of the present invention. In one embodiment, the method comprises (a) isolating membranes from cultured cells selected from the group consisting non specific cytotoxic cells obtainable from a teleost fish or mammalian monocytes or mammalian macrophages and (b) isolating said polypeptide from said isolated membranes of (a).

The polypeptide of the present invention may also be obtained by (a) isolating membranes from cultured cells selected from the group consisting non specific cytotoxic cells obtainable from a teleost fish, mammalian macrophages or mammalian monocytes;

(b) combining said membranes with the antibody of the present invention and (c) isolating a compound from said membranes that bound to said antibody.

The method further comprises and additional step prior to step(a) of culturing nonspecific cytotoxic cells obtainable from teleosts or mammalian macrophages or monocytes. The method may further comprise after step (b) determining if said isolated polypeptide binds to oligoguanosine and/or has antimicrobial activity.

Alternatively, the polypeptide of the present invention may be obtained by (a) culturing one or more host cells comprising a nucleic acid encoding said polypeptide and (b) isolating said polypeptide from said cultured cells of (a).

DEFINITIONS

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984,"Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Furthermore, the following terms shall have the definitions set out below.

As defined herein "isolated" refers to material removed from its original environment and is thus altered "by the band of man" from its natural state.

The amino acid residues described herein are preferred to be in the "L" isomeric form. However, residues in the "D"

isomeric form can be substituted for any L-amino acid residue, as long as the desired functionality is retained by the polypeptide. $NH_2$ refers to the free amino group present at the amino terminus of a polypeptide. COOH refers to the free carboxy group present at the carboxy terminus of a polypeptide.

"Nucleic acid construct" is defined herein, is a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence of the present invention.

The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5'-end of the mRNA and a transcription terminator sequence located just downstream of the open reading frame at the 3'-end of the mRNA. A coding sequence can include, but is not limited to, DNA, cDNA, and recombinant nucleic acid sequences.

A "heterologous" region of a recombinant cell is an identifiable segment of nucleic acid within a larger nucleic acid molecule that is not found in association with the larger molecule in nature.

An "expression vector" may be any vector (e.g., a plasmid or virus) which can be conveniently subjected to recombinant DNA procedures and can bring about the expression of the nucleic acid sequence.

An "origin of replication" refers to those DNA sequences that participate in DNA synthesis.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation, as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence. Transcriptional and translational control sequences are DNA regulatory sequences, such as promoters, enhancers, polyadenylation signals, terminators, and the like, that provide for the expression of a coding sequence in a host cell.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

It should be appreciated that also within the scope of the present invention are nucleic acid sequences encoding the polypeptide(s) of the present invention, which code for a polypeptide having the same amino acid sequence as the sequences disclosed herein, but which are degenerate to the nucleic acids disclosed herein. By "degenerate to" is meant that a different three-letter codon is used to specify a particular amino acid.

An "allelic variant" as defined herein is an alteration in the sequence of the gene having high homology to the original gene sequence.

As used herein, "epitope" refers to an antigenic determinant of a polypeptide. An epitope could comprise 3 amino acids in a spatial conformation which is unique to the epitope. Generally an epitope consists of at least 5 such amino acids, and more usually, consists of at least 8-10 such amino acids. Methods of determining the spatial conformation of amino acids are known in the art, and include, for example, x-ray, crystallography and 2-dimensional nuclear magnetic resonance.

A polypeptide is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The techniques for determining whether a polypeptide is immunologically reactive with an antibody are known in the art.

An "antibody" is any immunoglobulin, including antibodies and fragments thereof, that bind a specific epitope. The term encompasses polyclonal, monoclonal, and chimeric antibodies; the last mentioned described in further detail in U.S. Pat. Nos. 4,816,397 and 4,816,567.

Fab and F(ab')$_2$ fragments are prepared by the proteolytic reaction of papain and pepsin, respectively, on substantially intact antibody molecules by methods that are well-known. See for example, U.S. Pat. No. 4,342,566. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

A nucleic acid molecule is "operatively linked" to an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

The term "stringent hybridization conditions" are known to those skilled in the art and can be found in Current Protocols in Molecular Biology, John Wiley & Sons, N.Y. (1989), 6.3.1-6.3.6. A preferred, non-limiting example of stringent hybridization conditions is hybridization in 6× sodium chloride/sodium citrate (SSC) at about 45° C., followed by one or more washes in 0.2.×SSC, 0.1% SDS at 50° C., preferably at 55° C., and more preferably at 60° C. or 65° C.

As used herein, "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, PCT application WO95/11995, Lockhart et al. (1996; Nat. Biotech. 14: 1675-1680) and Schema et al. (1996; Proc. Natl. Acad. Sci. 93: 10614-10619). In other embodiments, such arrays are produced by the methods described by Brown et al., U.S. Pat. No. 5,807,522.

The term "antimicrobial", as used herein, refers to the ability to slow, reduce, terminate or inhibit the growth of microorganisms. Microorganisms which may be treated with compounds of the present invention include, but are not limited to, fungi, parasites, bacteria, protozoa, etc.

The term "lysine-rich motifs" or "lysine box motifs" as used herein, refers to the periodic expression of lysine characterized by: KxxxK, KKxxK and KxxKK where x is a non lysine residue.

BRIEF DESCRIPTION OF THE FIGURES

FIG. 4 shows dG20 (SEQ ID NO:6) binds to low molecular weight proteins. FIG. 4A shows a membrane preparation of anterior kidney NCC resolved by SDS-PAGE and transferred onto nitrocellulose. Ligand blotting was accomplished by adding: lane 1, dG20 (SEQ ID NO:6)-biotin (1 µg/ml); lane 2, dA20 (SEQ ID NO:9)-biotin (1 µg/ml); lane 3, Neutravidin-peroxidase conjugate; lane 4, rabbit polyclonal anti-ncamp-1; lane 5, pre-immune rabbit serum; and lane 6 goat anti-rabbit HRP conjugate control. FIG. 4B shows immunoprecipitates resolved on a 12.5% gel, transferred to nitrocellulose and probed with ExtrAvidin-peroxidase. FIG. 4C shows anterior kidney NCC membrane preparations resolved on a 12.5% gel and transferred onto nitrocellulose and subjected to Western blotting with biotinylated (polyclonal) anti-histone H1 antibody (lane 1) followed by ExtrAvidin-peroxidase each for 1 h or ExtrAvidin-peroxidase alone (lane 2) for 1 h.

FIG. 5 shows dG20 (SEQ ID NO:6) binding to RAW264.7 is not competitively inhibited by anti-Scavenger receptor (SR) antibody.

FIG. 6 shows binding of dG20 (SEQ ID NO:6) to NCC up-regulates the expression of the homologous receptor. Purified NCC ($1 \times 10^6$ cells/ml) were incubated with dG20 (SEQ ID NO:6) (50 µg/ml) (solid square), PMA/A23187 (0.5 µg/ml and 2.5 µg/ml respectively) (solid triangle) and media (solid circle) for the indicated time periods. At each time point $1 \times 10^5$ cells were harvested, washed with cold PAB and incubated with dG20-biotin (SEQ ID NO:6) for 1 h followed by the addition of Extravidin-PE conjugate for 30 min on ice. Cells were analyzed by flow cytometry. Percent positive cells (A) and mean fluorescence intensities (MFI) (B) at each time point are shown. Data are representative of three independent experiments. Insert (A): Histogram showing MFI of dG20 (SEQ ID NO:6) binding on NCC at 0 h (closed histogram) and after 36 h of dG20 treatment (open histogram).

FIG. 10 shows compiled full-length catfish NCAMP-1 cDNA sequence (depicted in SEQ ID NOS 3-5). Lysine residues are represented in bold letters. Polyadenylation site is highlighted and poly A tail is underlined. Start and stop codons also are represented in bold letters.

FIG. 11 shows comparisons of the deduced amino acid sequence of catfish DNA (SEQ ID NO:3) binding protein with histone H1 proteins from different species (zebrafish (*Danio rerio*) (SEQ ID NO:12), *Xenopus* (SEQ ID NO:13), mouse (SEQ ID NO:14) and human (SEQ ID NO:15)). Boxed area was also identified from primary sequencing and was the source for design of original degenerate primers. Multiple sequence alignment comparisons were made using CLUSTAL W.

FIG. 13 shows that the catfish histone H1X-like ODN binding protein was expressed in *E. coli* as a 6× His-tagged recombinant.

FIG. 14 shows polyclonal anti-NCAMP-1 binds NCC and recognizes a 29 Da protein in NCC membrane lysates.

FIG. 15 shows anti-NCAMP-1 and oligodeoxynucleotide bind to the same protein on NCC. Catfish anterior kidney cells were examined by competition binding experiments. In FIG. 15A, the positive control anti-NCAMP-1 binds to NCC; addition of dA20 (SEQ ID NO:9) prior to anti-NCAMP-1 does not prevent antibody binding; and GpC-Biotin (SEQ ID NO:11) prevents anti-NCAMP-1 binding. In FIG. 15B, reciprocal binding competition between GpC (SEQ ID NO:11) and anti-ncamp-1 demonstrates the same binding specificities. In FIG. 16B, the appropriate controls are shown.

FIG. 16 shows identification of lysine-rich motifs in the N-CAMP-1 and comparisons with other antimicrobial proteins for N-terminal residues of NCAMP-1 (amino acid residues 10-50 of SEQ ID NO:3); H1-Mus (SEQ ID NO: 16); H1-Human (SEQ ID NO:17) (Rose et al., 1998, Inf. Immun. 66: 3255-3263); H1-Trout (SEQ ID NO:18) (Fernandes et al., 2002. Biochem. J. 368:611-620) and C-terminal residues of NCAMP-1 (amino acid residues 139-198 of SEQ ID NO:3); H2A-CF (SEQ ID NO:19) (Park et al., 1998, FEBS Lett. 437:258-262); H2B Trout (SEQ ID NO:20) (Robinette et al., 1998, Cell Mol Life Sci, 54:467-475); H2B Bass1 (SEQ ID NO:21) (Noga et al., 2001, Parasitol. 123:57-65); H2B Bass2 (SEQ ID NO:22) (Noga et al., 2001, Parasitol. 123:57-65; Kootstra et al., 1978, Biochem. 17:2504-2510); H1-Trout (amino acids 1-20 of SEQ ID NO:23) (Macleod et al., 1977, Eur. J. Biochem., 78:281-291); H1-Trout (SEQ ID NO:23) (Noga et al., 2001, Parasitol. 123:57-65 and Patrzykat et al., 2001, Antimicrob. Agents Chemother. 45:1337-1342).

DETAILED DESCRIPTION OF THE INVENTION

Figure 1A:
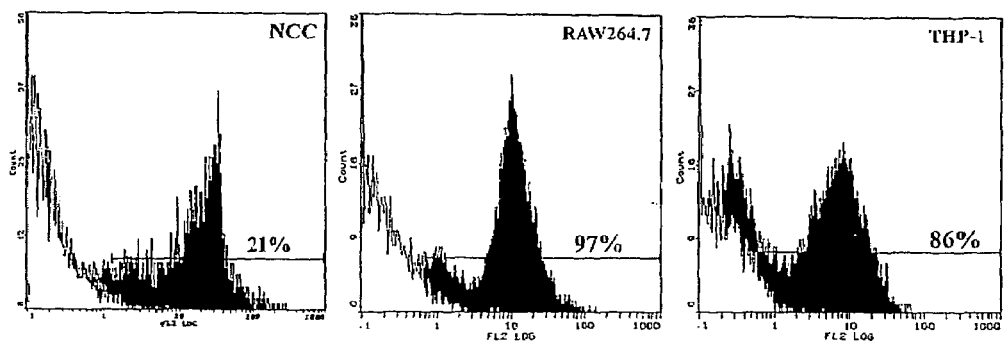
FIG. 1A shows dG20 (SEQ ID NO:6) binds to NCC, RAW264.7 and THP-1.

The invention further relates to an antimicrobial polypeptide having at least about 90% identity to a polypeptide comprising SEQ ID NO:3. Percent identity is generally determined by aligning the residues of the two amino acid sequences (i.e., a candidate amino acid sequence and the amino acid sequence of SEQ ID NO:3) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate amino acid sequence is the amino acid sequence being compared to an amino acid sequence present in a preferred polypeptide of the present invention. Preferably, two amino acid sequences are compared using the GAP program of the GCG Wisconsin Package (Genetics Computer Group, Madison, Wis.) version 10.0 (update January 1999). The GAP program uses the algorithm of Needleman and Wunsch (J. Mol. Biol., 48:443453 (1970) to find the alignment of two complete sequences that maximizes the number of matches and minimizes the number of gaps. Preferably, the default values for all GAP search parameters are used, including scoring matrix—BLOSUM62.cmp, gap weight=8, length weight2, average match=2.912, and average mismatch=−2.003. In the comparison of two amino acid sequences using the GAP search algorithm, structural similarity is referred to as "percent identity." Preferably, a polypeptide includes an amino acid sequence having a structural similarity with SEQ ID NO:3 of at least about 90 or 95%, more preferably at least about 97%, 98% most preferably at least about 99% identity.

The polypeptide sequences of the present invention can further be used as a "query sequence" to perform a search against sequence databases to, for example, identify other family members or related sequences. Such searches can be performed using the NBLAST and XBLAST programs (version 2.0) of Altschul, et al. (J. Mol. Biol. 215:403-10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (Nucleic Acids Res. 25:3389-3402 (1997)). When utilizing BLAST and gapped BLAST programs, the default parameters of the respective programs (e.g., XBLAST and NBLAST) can be used.

Allelic variants of the polypeptide of the present invention can readily be identified as being a human protein having a high degree (significant) of sequence homology/identity to at least a portion of the secreted peptide as well as being encoded by the same genetic locus as the secreted peptide provided herein. As used herein, two proteins (or a region of the proteins) have significant homology when the amino acid sequences are typically at least about 70-80%, 80-90%, and more typically at least about 90-95% or more homologous. A significantly homologous amino acid sequence, according to the present invention, will be encoded by a nucleic acid sequence that will hybridize to a secreted peptide encoding nucleic acid molecule under stringent conditions as more fully described below.

Paralogs of a the polypeptide of the present invention can readily be identified as having some degree of significant amino acid sequence homology/identity to at least a portion of the secreted peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a secreted peptide encoding nucleic acid molecule under moderate to stringent conditions as more fully described below.

Orthologs of a secreted peptide can readily be identified as having some degree of significant sequence homology/identity to at least a portion of the secreted peptide as well as being encoded by a gene from another organism. Preferred orthologs will be isolated from mammals, preferably primates, for the development of human therapeutic targets and agents. Such orthologs will be encoded by a nucleic acid sequence that will hybridize to a secreted peptide encoding nucleic acid molecule under moderate to stringent conditions, as more fully described below, depending on the degree of relatedness of the two organisms yielding the proteins.

Nucleic Acid Molecules

As stated above, the present invention also relates to a nucleic acid molecule, particularly a recombinant DNA molecule or cloned gene, or a degenerate variant thereof, which encodes an antimicrobial teleost-like polypeptide, or a fragment thereof, that possesses an amino acid sequence as set forth herein, including the sequences or a portion thereof of as described herein, particularly as embodied in SEQ ID NO:3, respectively. In particular, the nucleic acid molecule of the present invention is substantially identical to a nucleic acid molecule comprising SEQ ID NO:4 or its reverse complement.

As defined herein, "substantially identical" means it has at least 80% identity to said region and/or sequence, It may also have 85%, 90%, 95%, 97%, 98%, and 99% identity. The length of sequence identity comparison may be over a stretch of at least about nine nucleotides, usually at least about 20 nucleotides, more usually at least about 24 nucleotides. As a practical matter, whether any particular nucleic acid molecule is at least 80%, 85%, 90%, 95%, 96%, 97%, 98% or 99% identical to a nucleotide sequence of the present invention.

The comparison of sequences and determination of percent identity and similarity between two sequences can be accomplished using a mathematical algorithm. (Lesk, A. M., ed., 1988, Computational Molecular Biology, Oxford University Press, New York; Smith, D. W., ed., 1993, Biocomputing: Informatics and Genome Projects, Academic Press, New York; Griffin, A. M., and Griffin, H. G., eds, 1994, Computer Analysis of Sequence Data, Part 1, Humana Press, New Jersey; von Heinje, G., 1987, Sequence Analysis in Molecular Biology, Academic Press; and Gribskov, M. and Devereux, J., eds., 1991, Sequence Analysis Primer, M Stockton Press, New York). In a preferred embodiment, the percent identity between two amino acid sequences is determined using the Needleman and Wunsch (1970, J. Mol. Biol. 48:444-453) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux et al., 1984, Nucleic Acids Res. 12:387) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of Myers and Miller (1989, CABIOS, 4:11-17) which has been incorporated into the ALIGN program (version 2.0), using a PAM120 weight residue table, a gap length penalty of 12 and a gap penalty of 4.

The nucleic acid sequences of the present invention can further be used as a "query sequence" to perform a search against sequence databases to, for example, identify other family members or related sequences. Such searches can be performed using the NBLAST and XBLAST programs (version 2.0) of Altschul, et al. (1990, J. Mol. Biol. 215:403-410). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (1997, Nucleic Acids Res. 25:3389-3402). When utilizing BLAST and gapped BLAST programs, the default parameters of the respective programs (e.g., XBLAST and NBLAST) can be used.

The invention is further directed to a nucleic acid construct comprising expression control sequences and nucleic acid molecules of the present invention. The nucleic acid sequence encoding the desired polypeptide, whether in fused or mature form, and whether or not containing a signal sequence to permit secretion, may be ligated into expression vectors suitable for any convenient host. The vector includes a plasmid, single or double stranded phage, a single or double stranded RNA or DNA viral vector, or artificial chromosome, such as a BAC, PAC, YAC, or MAC.

Microarrays and Kits

The microarray generally contains a large number of unique, single-stranded nucleic acid sequences, fixed to a solid support, wherein at least one of which is a nucleic acid hybridizing to at least a 10 nucleotide fragment, more preferably at least about a 20 nucleotide fragment of a nucleic acid encoding the polypeptide of the present invention. The fragment may be a derived from a noncoding or coding region of the nucleic acid of the present invention, encoding the antimicrobial polypeptide of the present invention. The oligonucleotides may be about 10-60 nucleotides in length. Alternatively larger fragments, e.g., of about 50, 70, 75, 150, 500, 600, 750, 800, 850, 900 or about 950 nucleotides in length may be used. In yet another embodiment, BAC or YAC arrays may be used containing full length cDNA or genomic sequences.

In order to produce oligonucleotides to a known sequence for a microarray or detection kit, the nucleic acid of interest is typically examined using a computer algorithm which starts at the 5' or at the 3' end of the nucleotide sequence. Typical algorithms will then identify oligomers of defined length that are unique to said nucleic acid, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a solid support using a light-directed chemical process. The solid support may be paper, nylon or other type of membrane, filter, chip, glass slide or any other suitable solid support.

The microarrays of the present invention may be used to identify nucleic acids encoding the polypeptides of the present invention from a biological sample. Such a sample includes but is not limited to non specific cytotoxic cells from a teleost fish, mammalian macrophages and moncytes or in a specific embodiment from membrane fractions from said cells.

In another embodiment, the invention is directed to a kit comprising at least one nucleic acid comprising at least 10 nucleotides hybridizing under stringent conditions to a coding or noncoding region of a nucleic acid encoding the antimicrobial polypeptide of the present invention. In a more specific embodiment, the kit comprises a probe or primer comprising 50, 70, 75, 150, 500, 600, 750, 800, 850, 900 or about 950 nucleotides in length may be used. In yet another embodiment, BAC or YAC arrays may be used containing full length cDNA or genomic sequences. The nucleic acid may act as a probe or primer and may be labeled with a detectable label. The detectable label may, for example, be a radioactive label, fluorescer, antibody or enzyme. The kit may further comprise the label. Alternatively, the kit may comprise a microarray. The probes or primers of the present invention may act as a primer to synthesize further nucleic acid probes.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments disclosed herein. Examples of such assays can be found in Chard, 1986, An Introduction to Radioimmunoassay and Related Techniques, Elsevier Science Publishers, Amsterdam, The Netherlands; Bullock, G. R. et al., Techniques in Immunocytochemistry, Academic Press, Orlando, Fla. Vol. 1 (1982), Vol. 2 (1983), Vol. 3 (1985); Tinsel, Practice and Theory of Enzyme Immunoassays: Laboratory Techniques in Biochemistry and Molecular Biology, Elsevier Science Publishers, Amsterdam, The Netherlands (1985).

Production of Polypeptides

If the isolated nucleic acid of the present invention is an RNA sequence, a cDNA sequence may be obtained and used to produce a recombinant polypeptide of the present invention comprising a heterologous sequence using methods known in the art. Both eukaryotic and prokaryotic host systems are presently used in forming recombinant polypeptides. The polypeptide is then isolated from lysed cells or from the culture medium and purified to the extent needed for its intended use. Purification may be by techniques known in the art, for example, differential extraction, salt fractionation, chromatography on ion exchange resins, affinity chromatography, centrifugation, and the like. See, for example, Methods in Enzymology for a variety of methods for purifying proteins. Both prokaryotic and eukaryotic host cells may be used for expression of desired coding sequences when appropriate control sequences, which are compatible with the designated host, are used. Bacterial cells include, but are not limited to, *E. coli, Streptomyces*, and *Salmonella typhimurium*. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These markers may be used to obtain successful transformants by selection. Commonly used prokaryotic control sequences include the Beta-lactamase (penicillinase) and lactose promoter systems, the tryptophan (trp) promoter system and the lambda-derived $P_L$ promoter and N gene ribosome binding site and the hybrid TAC promoter derived from sequences of the trp and lac UV5 promoters. The foregoing systems are particularly compatible with *E. coli*; if desired, other prokaryotic hosts such as strains of *Bacillus* or *Pseudomonas* may be used, with corresponding control sequences.

Eukaryotic cells include, but are not limited to, yeast, insect cells such as *Drosophila*, animal cells such as COS and CHO cells, and plant cells. *Saccharomyces cerevisiae* and *Saccharomyces carlsbergensis* are the most commonly used yeast hosts, and are convenient fungal hosts. Yeast compatible vectors carry markers that permit selection of successful transformants by conferring prototrophy to auxotrophic mutants or resistance to heavy metals on wild-type strains. Yeast compatible vectors may employ the 2 micron origin of replication, the combination of CEN3 and ARS1 or other means for assuring replication, such as sequences which will result in incorporation of an appropriate fragment into the host cell genome. Examples of vectors for expression in yeast e.g., *S. cerevisiae* include pYepSec1 (Baldari, et al., 1987, EMBO J. 6:229-234; pMFa (Kuijan et al., 1982, Cell 30:933-943), pJRY88 (Schultz et al., 1987, Gene 54:113-123), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., 1983, Mol. Cell Biol. 3:2156-2165) and the pVL series (Lucklow et al., 1989, Virology 170:31-39).

Mammalian cell lines available as hosts for expression are known in the art and include many immortalized cell lines available from the American Type Culture Collection (ATCC), including HeLa cells, Chinese hamster ovary (CHO) cells, baby hamster kidney (BHK) cells, and a number of other cell lines. Suitable promoters for mammalian cells are also known in the art and include viral promoters such as that from Simian Virus 40 (SV40), Rous sarcoma virus (RSV), adenovirus (ADV), and bovine papilloma virus (BPV). Mammalian cells may also require terminator sequences and poly A addition sequences; enhancer sequences which increase expression may also be included, and sequences which cause amplification of the gene may also be desirable. These sequences are known in the art.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the nucleic acid molecules of this invention on fermentation or in large scale animal culture.

As mentioned above, a DNA sequence encoding an antimicrobial protein of the present invention can be prepared synthetically rather than cloned. The DNA sequence can be designed with the appropriate codons for the antimicrobial protein amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, 1981, Nature, 292:756; Nambair et al., 1984, Science 223:1299; Jay et al., 1984, J. Biol. Chem. 259:6311.

The antimicrobial polypeptides of the present invention may also be obtained from non specific cytotoxic cells from teleosts which may include but are not limited to catfish, zebrafish. In a specific embodiment, the polypeptides of the present invention may be obtained by extracting said polypeptides from membranes of said nonspecific cytotoxic cells as described in the examples herein. The polypeptide of the present invention is identified by methods known in the art that include but are not limited to Western Blot analysis using an antibody to N-CAMP-1 or detecting binding to a labeled oligonucleotide such as GpC (SEQ ID NO:11) and/or oligoguanosine. The polypeptide of the present invention may be isolated by excision from a gel and purified by chromatography (e.g., affinity and/or RPLC). In a specific embodiment, the affinity column may have an antibody to said polypeptide attached to said column.

The activity of the isolated polypeptide(s) may be isolated using methods known in the art. These methods include but are not limited to assays known to assess antimicrobial activity, for example against *E. coli, Streptococcus iniae* and/or *M. luteus* and also such as those described in the examples herein.

Peptide Libraries

The polypeptides of the present invention may be used to generate a library of molecules that act as ligands for a specified target, single base oligonucleotides, particularly oligodeoxyguanosine, teleost non specific cytotoxic cells and/or GpC (SEQ ID NO:11). See, e.g., Kohl et al., 1993, Science 260: 1934. Techniques for constructing and screening such libraries are well known in the art. Peptide libraries may be synthesized on solid supports, or expressed on the surface of bacteriophage viruses (phage display libraries). Techniques are known in the art for screening synthesized molecules to select those with the desired activity, and for labeling the members of the library so that selected active molecules may be identified. See, e.g., Simon et al., 1992, Proc. Natl. Acad. Sci. USA 89: 9367; U.S. Pat. No. 5,283,173 (use of genetically altered *Saccharomyces cerevisiae* to screen peptides for interactions).

Antibodies

The polypeptide(s) of the present invention may be used to generate antibodies that specifically bind to said polypeptide(s). Examples of such antibodies include, but are not limited to, polyclonal, monoclonal, chimeric, single chain, Fab fragments, and fragments produced by a Fab expression library.

Various hosts may be used and include but are not limited to goats, rabbits, rats, mice, humans, and others. These hosts may be immunized by injection with the polypeptides of the present invention or any fragment or oligopeptide thereof which has immunogenic properties (e.g., 5-10 peptide fragments with immunogenic properties). Various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are especially preferable in humans.

Monoclonal antibodies to the said polypeptides and peptides of the present invention may be prepared using any technique which provides for the production of antibody molecules by continuous cell lines in culture. These include, but are not limited to, the hybridonma technique, the human B-cell hybridoma technique, and the EBV-hybridoma technique. See, e.g., Kohler, et al., 1975, Nature, 256: 495-497; Kozbor et al., 1985, J. Immunol. Methods 81: 31-42; Cote et al., 1983, Proc. Natl. Acad. Sci. USA 80: 2026-2030; Cole et al., 1984, Mol. Cell Biol. 62: 109-120.

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between the polypeptide(s) of the present invention and its specific antibody.

Antibodies may be conjugated to a solid support suitable for a diagnostic assay (e.g., beads, plates, slides or wells formed from materials such as latex or polystyrene) in accordance with known techniques, such as precipitation. Antibodies may likewise be conjugated to detectable groups such as radiolabels (e.g. $^{35}S$, $^{125}I$, $^{131}I$), enzyme labels (e.g., horseradish peroxidase, alkaline phosphatase), and fluorescent labels (e.g., fluorescein) in accordance with known techniques.

Kits for determining if a sample contains the polypeptides of the present invention will include at least one reagent specific for detecting the presence or absence of said polypeptide. In one embodiment, the diagnostic kit comprises (a) an antibody which binds proteins of the present invention conjugated to a solid support and (b) a second antibody which binds peptides of the present invention conjugated to a detectable group. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. A second embodiment of a test kit comprises (a) an antibody as above, and (b) a specific binding partner for the antibody conjugated to a detectable group. Ancillary agents as described above may likewise be included. The test kit may be packaged in any suitable manner, typically with all elements in a single container along with a sheet of printed out instructions for carrying out the test.

Compositions

The nucleic acids, nucleic acid fragments, polypeptides, polypeptide fragments, antibodies, antibody derivatives, and antibody fragments of the present invention may be formulated into a composition. Formulations of the substances of the present invention into pharmaceutical compositions is well known in the art, and is further described in Gennaro (ed.), 2000, Remington: The Science and Practice of Pharmacy, 20th ed., Lippincott, Williams & Wilkins (2000); and Ansel et al., 1999, Pharmaceutical Dosage Forms and Drug Delivery Systems, 7th ed., Lippincott Williams & Wilkins Publishers.

Such a composition typically contains from about 0.1 to 90% by weight (such as about 1 to 20% or about 1 to 10%) of the nucleic acid, polypeptide or antibody of the invention in a pharmaceutically accepted carrier. Solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate, and alginic acid. Tablet binders that can be used include acacia, methylcellulose, sodium carboxymethylcellulose, polyvinylpyrrolidone (Povidone™), hydroxypropyl methylcellulose, sucrose, starch and ethylcellulose. Lubricants that can be used include magnesium stearates, stearic acid, silicone fluid, talc, waxes, oils, and colloidal silica.

Liquid formulations of the compositions for oral administration prepared in water or other aqueous vehicles can contain various suspending agents such as methylcellulose, alginates, tragacanth, pectin, kelgin, carrageenan, acacia, polyvinylpyrrolidone, and polyvinyl alcohol. The liquid formulations can also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

Injectable formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water soluble versions of the compounds can be administered by the drip method, whereby a pharmaceutical formulation containing the antifungal agent and a physiologically acceptable excipient is infused. Physiologically acceptable excipients can include, for example, 5% dextrose, 0.9% saline, Ringer's solution or other suitable excipients. Intramuscular preparations, e.g., a sterile formulation of a suitable soluble salt form of the compounds, can be dissolved and administered in a pharmaceutical excipient such as Water-for-Injection, 0.9% saline, or 5% glucose solution. A suitable insoluble form of the compound can be prepared and administered as a suspension in an aqueous base or a pharmaceutically acceptable oil base, such as an ester of a long chain fatty acid (e.g., ethyl oleate).

A topical semi-solid ointment formulation typically contains a concentration of the active ingredient from about 1 to 20%, e.g., 5 to 10%, in a carrier such as a pharmaceutical cream base. Various formulations for topical use include drops, tinctures, lotions, creams, solutions, and ointments containing the active ingredient and various supports and vehicles. The optimal percentage of the therapeutic agent in each pharmaceutical formulation varies according to the formulation itself and the therapeutic effect desired in the specific pathologies and correlated therapeutic regimens.

Conventional methods, known to those of ordinary skill in the art of medicine, can be used to administer compositions to the patient. These include but are not limited to enteral, subcutaneous, intrapulmonary, transmucosal, intraperitoneal, intrauterine, sublingual, intrathecal, or intramuscular routes) by using standard methods. In addition, the pharmaceutical formulations can be administered to the patient via injectable depot routes of administration such as by using 1-, 3-, or 6-month depot injectable or biodegradable materials and methods. The compositions may also be administered to the patient by applying to the skin of the patient a transdermal patch containing the pharmaceutical formulation, and leaving the patch in contact with the patient's skin (generally for 1 to 5 hours per patch). Other transdermal routes of administration (e.g., through use of a topically applied cream, ointment, or the like) can be used by applying conventional techniques.

Regardless of the route of administration, the substance of the present invention is typically is administered at a daily dosage of about 0.01 mg to about 30 mg/kg of body weight of the patient (e.g., 1 mg/kg to 5 mg/kg). The pharmaceutical formulation can be administered in multiple doses per day, if desired, to achieve the total desired daily dose.

The substances of the present invention along with other antimicrobial substances may also be formulated into compositions. Such antimicrobial substances include but are not limited to acyclovir, cecropin A, cecropin B, magainins, pleurocidin, cefaclor, cefadroxil, ciprofloxacin, erythromycin, penicillin, amoxcilin, or tetracycline.

The effectiveness of the method of treatment can be assessed by monitoring the patient for known signs or symptoms of a disorder.

Therapeutic Uses

Nucleic acids encoding the polypeptides of the present invention as well as the polypeptides of the present invention may be used as an antimicrobial agent. In a particular embodiment, the nucleic acids and polypeptides of the present invention may be used to treat disorders resulting from infection by Gram-negative and Gram-positive bacteria, parasites, protozoa and fungi.

Furthermore, these substances may be used to reverse the resistance of antibiotic-resistant bacteria, allowing them to once again become susceptible to conventional antibiotics which had previously been ineffective. Thus, the present invention provides a method of treating, reducing or combating antibiotic resistance in a bacteria, which bacteria is resistant to at least one antibiotic. The method comprises administering to the bacteria, in vitro or in vivo in a subject in need thereof, a compound of the present invention in an amount effective to reduce antibiotic resistance (e.g., render the bacteria susceptible to subsequent treatment or control with the antibiotic to which it was previously resistant). Examples of at least one antibiotic to which the bacteria may be resistant, include but are not limited to methicillin, vanconmycin, penicillin and streptogramin. Example bacteria which may be antibiotic resistant and may be treated by the method of the invention include but are not limited to *Staphylococcus aureus, Escherichia coli, Streptococcus faecalis, Klebsiella pneumoniae, Pseudomonas aeruginosa*, and *Shigella flexneri*.

Additionally, as noted about, these substances may be administered sequentially or simultaneously with other antibiotics.

EXAMPLES

The following Examples are provided to illustrate the present invention and should not be construed as limiting thereof.

Example 1

Single Base Oligodeoxyguanosine Binding Proteins on Nonspecific Cytotoxic Cells: Identification of a New Class of Pattern Recognition Receptors Membrane proteins have been identified on teleost nonspecific cytotoxic cells (NCC) and mammalian cells that bind single base oligodeoxynucleotide (ODN) ligands. These ODNs contain 20-mers of guanosine (dG20) (SEQ ID NO:6), adenosine (dA20) (SEQ ID NO:9), thymidine (dT20) (SEQ ID NO: 10) or cytosine (dC20) (SEQ ID NO:8). ODNs were first examined for binding to NCC and to (mouse) RAW 264.7 and (human) THP-1 cells. Binding to NCC by dG20 (SEQ ID NO:6) was specific and saturable at 1.25 µg/ml. Saturable binding to RAW and THP-1 cells by dG20 (SEQ ID NO:6) occurred at 0.2 µg/ml and 0.8 µg/ml (respectively). dG20 (SEQ ID NO:6) bound to NCC in the anterior kidney (i.e. fish bone marrow equivalent), spleen and liver. Ligand blots of NCC membrane lysates with biotinylated-dG20 (SEQ ID NO:6) revealed 16-18 and 29 kDa binding proteins. The 29 kDa protein was further identified by Western blot analysis using polyclonal anti-NCC antimicrobial protein-1 (NCAMP-1) antibodies. The membrane expression of the 29 kDa NCAMP-1 was also identified by immunoprecipitation (with anti-digoxigenin-agarose beads) of complexes composed of digoxigenin-dG20-biotinylated (SEQ ID NO:6) NCC membrane proteins. NCAMP-1 and 14-18 kDa NCC membrane proteins were crossreactive by Western blot examination with a polyclonal anti-histone-1 antibody. Function studies revealed that dG20 (SEQ ID NO:6) activated a 2-fold upregulation of membrane binding of homologous dG20-biotin(SEQ ID NO:6). dG20 (SEQ ID NO:6) also stimulated NCC increased membrane expression of NCC receptor protein-1 (NCCRP-1). Additional experiments were conducted to determine the DNAse sensitivity of the different ODNs. dG20 (SEQ ID NO:6) appeared to be more resistant to DNase treatment compared to dC20(SEQ ID NO:8), dA20 (SEQ ID NO:9) and dT20 (SEQ ID NO: 10).

Material and Methods

Animals

*Ictalurus punctatus* (catfish) of both sexes, were obtained from local commercial farms. Fish were maintained in flow-through 300 gallon aquaria at ambient temperature (17-25° C.) and fed commercial fish pellets (Purina Catfish Startena, Ralston Purina Co., St. Louis, Mo.). Water quality was monitored for temperature, nitrite, ammonia nitrogen and chlorine contents.

Media, Reagents, Cells and Anitibodies

The murine macrophage-like cell line, RAW264.7, and human monocytic cell line, THP-1, were originally obtained from American Type Culture Collection (ATCC, Bethesda, Md.). NCC were prepared from anterior kidney (AK) of catfish. Cells were cultured in RPMI-1640 (Cellgro, Media Tech, Washington, D.C.) supplemented with L-glutamine, sodium pyruvate, EM vitamin solution, MEM amino acid solution, MEM non-essential solution (Cellgro), 50 mg/ml gentamicin (Schering-Plough Animal health Corp., Kenilworth, N.J.) and 10% fetal bovine serum (FBS, Atlanta biologicals, Norcross, Ga.). Washing media (PAB) consisted of 1×phosphate buffer saline (PBS), 0.1% sodium azide (Sigma Chemical Co., St. Louis, Mo.) and 1% bovine serum albumin (Sigma Chemical Co.). Calf thymus DNA, Phorbol 12-Myristate 13-Acetate (PMA, #P8139), calcium ionophore-A23187 (#C7522), DNase I (#D4263), Extravidin-phycoerythrin (PE) conjugate (#E4011) and ExtrAvidin-Peroxidase Conjugate (#E2886) were obtained from Sigma Chemical Co. Monoclonal (mab) antibody 5C6 (IgM isotype) specific for a 32-kDa NCC activation receptor protein (NC-CRP-1) was prepared in house (Evans et al., 1988, J. Immunol. 141:324-32). Unconjugated (#1322) and FITC conjugated (#1322F) forms of rat anti-mouse scavenger receptor antibody (SR-AI/II) 2F8 were purchased from Serotec Inc. (NC, USA). The isotype rat anti-mouse IgG2b-FITC was purchased from Southern Biotechnology Associates Inc. (Birmingham, Ala.). Anti-mouse IgM-FITC and biotin-IgM conjugates were obtained from Sigma Immunochemicals. Polyclonal anti-NCAMP-1 (NCC antimicrobial protein-1) was produced in rabbits and used with goat anti-rabbit IgG. This polyclonal recogilizes a recombinant protein previously shown to bind oligodeoxynucleotides, bacterial DNA and in recombinant form kills Gram negative and Gram positive bacteria.

Purification of NCC

Fish weighing 20-60 g were net captured and sacrificed by submersion in anesthetic (3-aminoenzoic acid ethyl ester; Sigma Chemical Co.). Anterior kidney (AK) tissue (mammalian bone marrow equivalent) was removed aseptically and passed through screen mesh to obtain single cell suspensions in complete RPMI-1640 containing 10% FBS. Cells were purified by density gradient centrifugation over a 45.5% Percoll (Sigma) cushion. Cells at the interface were collected, washed once with RPMI and resuspended in complete RPMI.

Oligodeoxynucleotides

Oligodeoxynucleotides were purchased from MWG-Biotech (High Point, N.C.). They were synthesized as phosphodiesters using standard methods and resuspended in endotoxin-free water. 5' end biotinylated (dG20-biotin (SEQ ID NO:6), dA20-biotin (SEQ ID NO:9) and dC20-biotin (SEQ ID NO:8)) and digoxigenin (DIG-dG20 (SEQ ID NO:6)) labeled ODNs were purchased from MWG-Biotech. The sequence, characteristics and size of each ODN are shown in Table 1.

TABLE 1

Sequence of the oligodeoxynucleotides.

| 5'-Oligodeoxynucleotides-3'[a] | Name |
|---|---|
| CCCCCCCCCCCCCCCCCCCC (SEQ ID NO: 8) | dC20 |
| AAAAAAAAAAAAAAAAAAAA (SEQ ID NO: 9) | dA20 |
| TTTTTTTTTTTTTTTTTTTT (SEQ ID NO: 10) | dT20 |
| GGGGGGGGGGGGGGGGGGGG (SEQ ID NO: 6) | dG20 |
| TCGTCGTTGTCGTTGTCGTT (SEQ ID NO: 7) | CpG |

[a]Non-biotinylated, 5' end biotinylated and digoxigenin conjugated forms of ODNs were also used in the study.

ODNs and calf thymus DNA were resuspended in endotoxin-free water. The endotoxin level was less than 0.015 endotoxin units (EU)/ml for all reagents used in the study as determined by Limulus Amebocyte lysate assay (kit #210-A; Sigma Chemical Co.).

Binding Assays

Purified NCC ($1\times10^6$/ml) were treated with dG20 (SEQ ID NO:6)-biotin (50 µg/ml) for 0 h and 36 h. Cells were washed and incubated with PAB for 1 h. $1\times10^5$ cells were stained with saturating amounts of mab 5C6 and dG20 (SEQ ID NO:6)-biotin for 1 h followed by washing twice with PAB and addition of anti-mouse-IgM-FITC (1:20 dilution) and Extravidin-PE conjugate (1:20 dilution) for 30 min. Cells were washed and analyzed by flow cytometry (two color analysis). Final resuspension of cells in all flow cytometric experiments was in 300 µl of PAB. For single color analysis of dG20 (SEQ ID NO:6)-biotin, $1\times10^5$ purified NCC or $5\times10^4$ RAW264.7 and THP-1 cells were incubated at 4° C. in PAB for 1 h followed by incubation with saturating amounts of dG20 (SEQ ID NO:6)-biotin for 1 h and Extravidin-PE for 30 min. Cells were washed and analyzed by flow cytometry. For SR expression on RAW264.7 cells, $2.5\times10^4$ cells were incubated with 100 µl of 5 µg/ml of FITC conjugated anti-SR antibody 2F8 for 1 h, washed and analyzed by flow cytometry. To determine the saturating amounts of dG20 (SEQ ID NO:6), $1\times10^5$ purified NCC or $5\times10^4$ RAW264.7 and THP-1 cells were incubated (PAB/4° C.) with 100 µl of different concentrations of dG20 (SEQ ID NO:6)-biotin for 1 h. Cells were washed twice with PAB and further incubated with Extravidin-PE conjugate for 30 min. Cells were washed and analyzed by flow cytometry.

Preparation of Cell Membranes

For membrane preparation, cells were washed three times with ice cold TBS (25 mM Tris-Cl, pH 7.5, 150 mM NaCl). Cells were resuspended in Dounce homogenization buffer (10 mM Tris-Cl, pH7.6, 0.5 mM $MgCl_2$, 10 µg/ml leupeptin, 10 µg/ml pepstatin and 1 mM PMSF) @$2\times10^7$ cells/ml and incubated on ice for 15 min. 333 µl of tonicity restoration buffer (10 mM Tris-Cl, pH 7.6, 0.5 MM $MgCl_2$ and 0.6 M NaCl) was added per ml of homogenization buffer and cells were spun at 500 g for 5 min. The supernatant fraction was collected and EDTA was added to 5 mM before centrifugation at 13000 rpm for 10 min. The pellet (equivalent to $1\times10^6$ cells) was washed twice with cold TBS containing 10 µg/ml leupeptin, 10 µg/ml pepstatin and 1 mM PMSF and finally resuspended in 100 µl of hot 1×SDS-sample buffer.

Competition Inhibition of dG20 Binding to NCC and RAW264.7

Cells ($2.5\times10^4$) were incubated with dA20 (SEQ ID NO:9), dC20 (SEQ ID NO:8), dG20 (SEQ ID NO:6), dT20 (SEQ ID NO:10), CpG (SEQ ID NO:7) ODN and anti-SR antibody 2F8 (in case of RAW264.7) for 1 h on ice. Concentration of unlabeled dG20 (SEQ ID NO:6), dA20 (SEQ ID NO:9), dC20 (SEQ ID NO:8) and dT20 (SEQ ID NO:10) was 1- to 1000-fold excess (NCC and RAW264.7) and that of CpG (SEQ ID NO:7) was 1- to 1000-fold excess (NCC) or 4- to 4000-fold excess (RAW264.7) of 50% saturating amounts of dG20 (SEQ ID NO:6)-biotin. For 2F8, 100 µl of following concentrations were used: 1 µg/ml, 2 µg/ml, 3 µg/ml and 4 µg/l per $2.5\times10^4$ cells were washed twice to remove excess unbound ODNs/antibody and incubated with 50% saturating amounts of dG20 (SEQ ID NO:6)-biotin for 1 h on ice. Cells were washed and further incubated for 30 min with Extravidin-PE conjugate and analyzed by flow cytometry.

Ligand Blot

NCC membrane proteins were resolved on a 12.5% SDS-PAGE gel and transferred onto nitrocellulose membrane at 100V for 1 h. Nitrocellulose filters were blocked with SuperBlock Dry Blend (TBS) blocking buffer (#37545, Pierce Chemical Co., Rockford, Ill.) containing 0.1% Tween for 30 min. Primary ligand incubation (dG20 (SEQ ID NO:6)-biotin and dA20 (SEQ ID NO:9)-biotin diluted in blocking buffer) was performed for 1 h, filters were washed with TBS containing 0.1% Tween-T (TBS-T) for 20 min (four times, 5 min each) and finally incubated with secondary conjugate (a 1:50,000 dilution of Neutravidin-peroxidase conjugate (Pierce Chemical Co.)] for 1 h. After washing with TBS-T for 20 min, detection was done with chemiluminiscent substrate (SuperSignal® West Pico Chemiluminescent, Pierce Chemical Co.).

Surface Labeling, Ligand-Precipitation and Blotting

NCCs were surface biotinylated using EZ-Link™ Sulfo-NHS-Biotin (#21217, Pierce Chemical Co.) according to manufacturer's instruction. Briefly, cells were washed three times with cold PBS, incubated with Sulfo-NHS-Biotin (50 µg/ml) ($1\times10^7$ cells/ml for 20 min at RT on rotator, washed four times with ice-cold PBS and lyzed with CHAPS lysis buffer (10 mM CHAPS, 0.15M NaCl, 10 mM Tris-Cl, pH 7.6, I mM EDTA) containing protease inhibitors (1 mM PMSF, 1 µM Leupeptin and 1 µM Pepstatin). NCC lysates prepared from surface biotinylated cells were subjected to ligand precipitation. For this, 200 µl of lysate was incubated for 2 h with 10 µg of DIG-dG20 (SEQ ID NO:6) at 4° C. followed by incubation with anti-digoxigenin-agarose beads (100 µl of slurry, #A-3827, Sigma Chemical Co.) for 2 h at 4° C. Beads were pelleted, washed and bound proteins were eluted with boiling in 1×SDS sample buffer. These proteins were resolved on 12.5% gel, transferred to nitrocellulose and probed with ExtrAvidin-peroxidase conjugate (1:15000) for 1 h. After washing with TBS-T for 20 min, detection was done with chemiluminescent substrate.

Western Blot

Anterior kidney NCC membrane preparations were resolved on 12.5% gel, transferred onto nitrocellulose membrane and probed with biotinylated anti-histone H1 antibody (#M20151S, Biodesign, Saco, Me.) (1 µg/ml) for 1 h. After washing with TBS-T for 20 min, filters were incubated with ExtrAvidin-peroxidase (1:50000) for 1 h, washed with TBS-T and proteins were detected with chemiluminescent substrate.

Receptor Expression

To determine NCCRP-1 receptor expression, purified NCC ($1\times10^6$/ml) were treated with different ODNs (50 μg/ml), calf thymus DNA (5 μg/ml) and PMA/A23187 (0.5 μg/ml/2.5 μg/ml) for various time periods. $1\times10^5$ cells were harvested, washed with PAB and stained with saturating concentrations of 5C6 mab for 1 h on ice. Cells were washed twice with PAB, incubated with anti-mouse FITC-IgM for 30 min on ice, washed and analyzed by flow cytometry. To determine ODN receptor expression, purified NCC ($1\times10^6$/ml) were treated with dG20 (SEQ ID NO:6) (50 μg/ml), PMA/A23187 (0.5 μg/ml /2.5 μg/ml) and media for different time periods as indicated. At each time point $1\times10^5$ cells were analyzed for ODN receptor expression. Cells were incubated in PAB for 1 h, pelleted, stained with saturating concentration of dG20 (SEQ ID NO:6)-biotin for 1 h on ice, washed twice followed by addition of Extravidin-PE for 30 min. Cells were washed and analyzed by flow cytometry.

DNAse Assay

For DNAse treatment, 15 μg of ODNs and 25 units of DNase I were dissolved together in 10 μl of 100 mM Tris-Cl (pH8) containing 5 mM $MgCl_2$ and incubated at 37° C. for 5 h. The mixture was heated at 95° C. for 5 min to inactivate the enzyme and chilled immediately. DNase I treated and non-treated ODNs were resolved on a 15% denaturing polyacrylamide gel at 180 v for 90 min. The gel was stained with ethidium bromide (0.5 μg/ml) for 30 min at room temperature. Gel pictures were obtained using a UV trans-illuminator.

Flow Cytometry

Flow cytometry analysis was performed using an EPICS XL-MCL four color analyzer (Coulter Electronics Corp, Hileah, Fla.), equipped with 15 mW air cooled argon-ion laser operating at 488 nm wavelength. Two-parameters, forward scatter (FS; size) and side scatter (SSc; granularity), and backgating were used to positively identify each cell population. 10,000 to 15,000 events were collected per sample. Conjugate controls were included to set the baseline fluorescence. FITC was detected using 525 nm bandpass filter by photomultiplier tube 1 (PMT1) and PE with 575 nm bandpass filter by photomultiplier tube 2 (PMT2). Isotype control antibodies were included to determine non-specific binding. Data was analyzed using Coulter's System II software, version 3.0.

Results

Single Base Oligodeoxyguanosine 20-mer Binds to NCC Mammalian Cells.

Figure 1B:
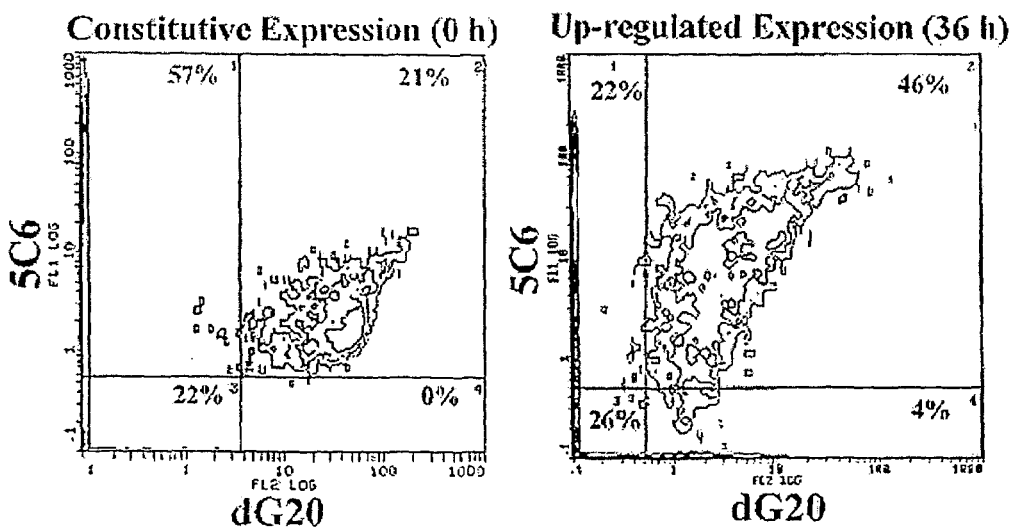
FIG. 1B shows constitutive levels and upregulated expression of dG20 (SEQ ID NO:6) binding. Histograms for conjugate alone (open) and cell specific (closed) dG20 (SEQ ID NO:6) binding are shown.

Experiments were first conducted to determine the cell type specificity and percentage positive cells of the dG20 (SEQ ID NO:6) constitutive binding levels. NCC were purified from the teleost bone marrow equivalent (i.e. the anterior kidney (AK)) and analyzed by flow cytometry for dG20 (SEQ ID NO:6) and mab 5C6 binding. This antibody (5C6) has been shown to recognize the NCC receptor NCCRP-1 (Evans et al., 1988, J. Immunol. 141:324-32.) 21% of NCC were positive for constitutive dG20 (SEQ ID NO:6) binding (FIGS. 1A and 1B).

Mammalian cell lines were evaluated for comparative binding to define whether dG20 (SEQ ID NO:6) "receptors" were unique to teleost cells. Purified NCC, RAW264.7 and THP-1 cells were incubated with PAB for 1 h/4° C. followed by incubation with saturating amounts of dG20-biotin for 1 h on ice and Extravidin-PE conjugate for 30 min. Cells were washed twice and analyzed by flow cytometry. Both cell lines THP-1 and RAW264.7 were 86% and 97% positive (respectively) for dG20 (SEQ ID NO:6) binding (FIG. 1A). Table 2 compares the binding of three single base ODNs to NCC, RAW 264.7 and THP-1 cells. Compared to dG20 (SEQ ID NO:6) the other two single base ODNs showed lower (dC20 (SEQ ID NO:8)) or negligible (dA20 (SEQ ID NO:9)) levels of binding.

TABLE 2

| ODN binding by NCC, RAW264.7 and THP-1 cells. | | | |
|---|---|---|---|
| ODN[a] | NCC | RAW264.7 | THP-1 |
| dG20 (SEQ ID NO: 6) | 21[b] | 96 | 87 |
| dC20 (SEQ ID NO: 8) | 14 | 17 | 2 |
| dA20 (SEQ ID NO: 9) | 2 | 1 | 1 |

[a]$1\times10^5$ cells were incubated with PAB for 1 h on ice followed by incubation with saturating concentrations of biotinylated ODNs for 1 h and Extravidin-PE conjugates for 30 min and analyzed by flow cytometry. Percent binding is shown. Data shown is representative of three independent experiments.
[b]The percentages shown were calculated by subtracting the control (background percent fluorescence) from the test binding. Background was usually less than 5%.

Two-color flow experiments were conducted with dG20 (SEQ ID NO:6)-activated NCC to determine the up-regulated dG20 (SEQ ID NO:6) receptor expression (FIG. 1B, right panel). Purified NCC were treated with dG20 (SEQ ID NO:6) for 0 h and 36 h and up-regulation of dG20 (SEQ ID NO:6) binding determined by two-color analysis. Cells were washed twice with PAB and stained with mab 5C6 and dG20 (SEQ ID NO:6)-biotin for 1 h followed by addition of FITC-anti-mouse-IgM and Extravidin-PE conjugates (30 min). Constitutive dG20 (SEQ ID NO:6) binding to NCC is shown in FIG. 1B (left panel). These data demonstrated that 26% and 67% (quadrant 2 as a percent of quadrant 1 plus 2) of purified NCC were positive for the dG20 (SEQ ID NO:6) binding at 0 h and 36 h respectively (FIG. 1B). ODN binding proteins on NCC can be up-regulated by dG20 (SEQ ID NO:6) stimulation.

Saturation and Specificity of dG20(SEQ ID NO:6) Binding.

Figure 2:
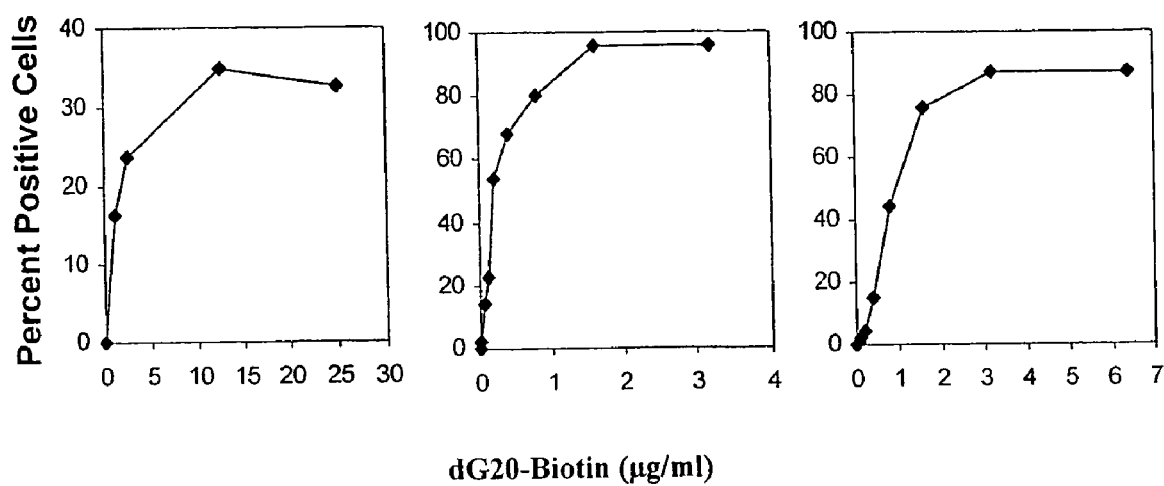
FIG. 2 shows saturation binding of dG20 (SEQ ID NO:6) to NCC, RAW264.7 and THP-1 cells. Percent binding is shown. Representative of three (NCC) or two (RAW264.7 and THP-1) independent experiments.

Binding experiments were next performed to determine whether binding by dG20 (SEQ ID NO:6) to NCC, RAW 264.7 and THP-1 was saturable and specific. Purified NCC or tissue cultured cells were incubated with different concentrations of dG20 (SEQ ID NO:6) (in PAB/4° C.) and percent positive binding was determined by flow cytometry (FIG. 2). $1\times10^5$ purified NCC, and $5\times10^4$ RAW264.7 and THP-1 were incubated with PAB for 1 h/4° C. followed by incubation with 100 ul of different concentrations of dG20 (SEQ ID NO:6)-biotin (as indicated) for 1 h on ice. Cells were washed twice with PAB and further incubated with Extravidin-PE conjugate (30 min) and analyzed by flow cytometry, percent saturation occurred at approximately 1.25 μg/ml NCC; 0.2 μg/ml RAW 264.7; and 0.8 μg/ml THP-1 cells.

Figures 3A, 3B, 3C, 3D:
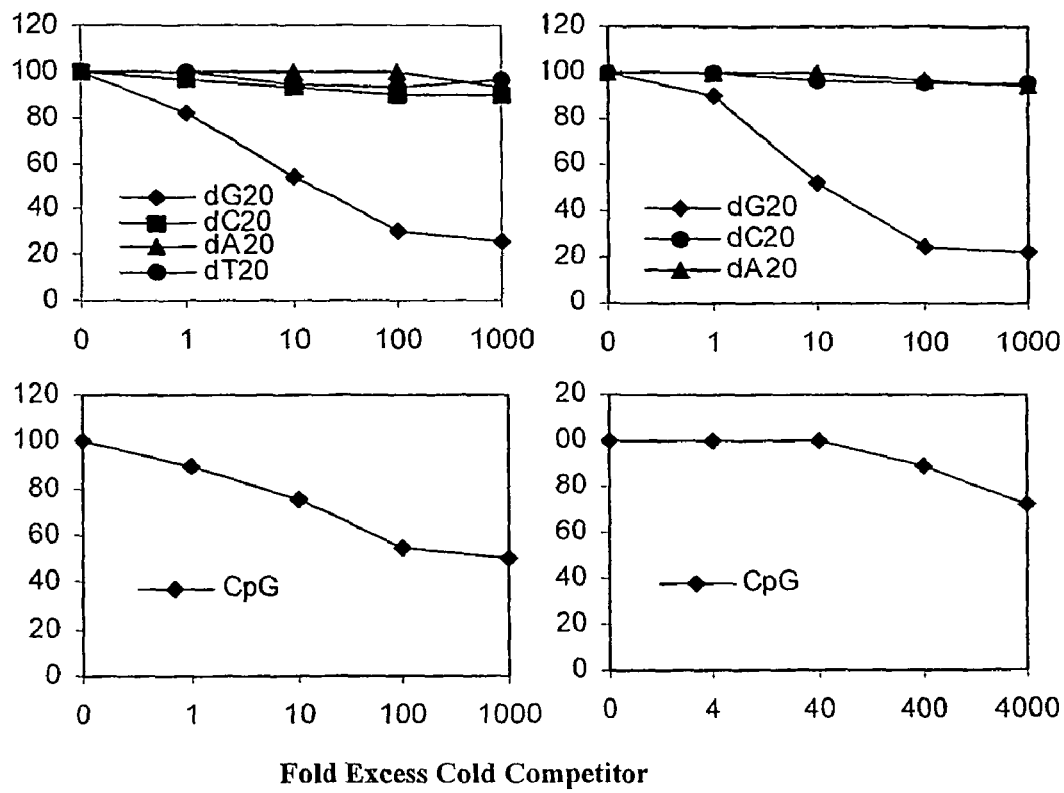
FIG. 3 shows dG20 (SEQ ID NO:6) binding to NCC and RAW264.7 cells is competitively inhibited by cold homologous dG20 (SEQ ID NO:6) and CpG (SEQ ID NO:7) but not by dC20 (SEQ ID NO:8) or dA20 (SEQ ID NO:9). $2.5 \times 10^4$ NCC (FIGS. 3A and B) or RAW264.7 (FIGS. 3C and D) were incubated with unlabeled dA2O (SEQ ID NO:9), dC20 (SEQ ID NO:8), dG20 (SEQ ID NO:6), dT20 (SEQ ID NO:10)and CpG ODN (SEQ ID NO:7) (fold-excess of cold ODN as indicated) for 1 h on ice. Data shown is representative of two independent experiments.

Specificity of binding was determined by "cold" competition assays. NCC and RAW264.7 cells were first incubated with different fold excess of soluble unlabeled ODNs (dG20 (SEQ ID NO:6), dA20 (SEQ ID NO:9), dT20 (SEQ ID NO:10) and dC20 (SEQ ID NO:8)). Cells were washed to remove excess unbound ODNs and incubated with 50% saturating amounts of dG20 (SEQ ID NO:6)-biotin for 1 h on ice. Cells were washed and further incubated for 30 min with Extravidin-PE conjugate and analyzed by flow cytometry. FIGS. 3A and 3C show that only unlabeled dG20 (SEQ ID NO:6) competed for binding with homologous ODN (dG20 (SEQ ID NO:6)-biotin) in NCC and RAW264.7. dG20 (SEQ ID NO:6) binding in both these cell types was reduced to <30% in the presence of unlabeled dG20 (SEQ ID NO:6). These results indicated that dG20 (SEQ ID NO:6) binding to NCC is saturable and specific. FIGS. 3B and 3D demonstrate that phosphodiester CpG (SEQ ID NO:7) partially competed for dG20 (SEQ ID NO:6) binding at much lower concentrations that those seen for RAW 264.7 cells. 50% inhibition occurred at approximately 100-fold CpG (SEQ ID NO:7)

competition whereas 4000 fold CpG (SEQ ID NO:7) was required to produce approximately 30% inhibition for RAW 264.7 cells.

Identification of dG20(SEQ ID NO:6) Binding Proteins

Purified NCC were lysed and membrane preparations were analyzed by SDS-PAGE and ligand and Western blots. FIG. 4A shows that dG20 (SEQ ID NO:6)-biotin (lane 1) but not dA20 (SEQ ID NO:8)-biotin (lane 2) or ExtrAvidin-peroxidase conjugate (lane 3) binds to the 29 kDa membrane protein. FIG. 4A also demonstrates binding of the same mw protein as dG20 (SEQ ID NO:6)-biotin by polyclonal anti-NCAMP-1 (lane 4). Lanes 5 and 6 are negative controls with pre-immune rabbit serum and conjugate (only) respectively. THP-1 and RAW264.7 had binding patterns of 14-18 and approximately 33 kDa binding proteins in dG20 (SEQ ID NO:6)-biotin ligand blots.

To confirm the membrane expression of these proteins, NCC were surface labeled with biotin, cell lysates were prepared followed by ligand precipitation with DIG-dG20 (SEQ ID NO:6) (DIG-dG20 (SEQ ID NO:6)-protein-biotin complex). Immunoprecipitation was next done using anti-digoxigenin agarose beads. Immunoprecipitates were resolved in 12.5% gels (FIG. 4B). An intense 29 kDa with faint 14 and 20 kDa signals were observed. A 66 kDa band was also observed in the control lane (data not shown) suggesting nonspecific binding.

Figure 5A:
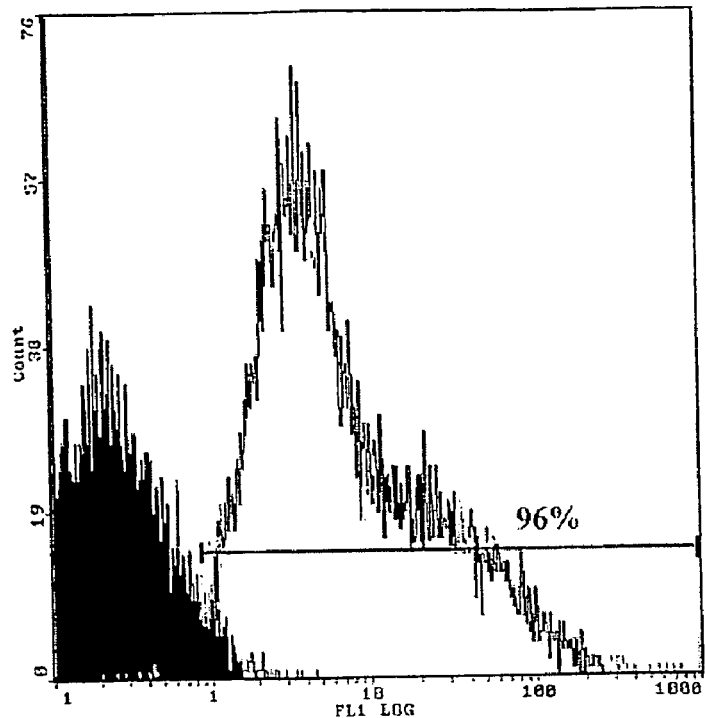
FIG. 5A shows an overlay histogram of anti-SR antibody (open) and isotype control antibody (closed) is shown.
Figure 5B:
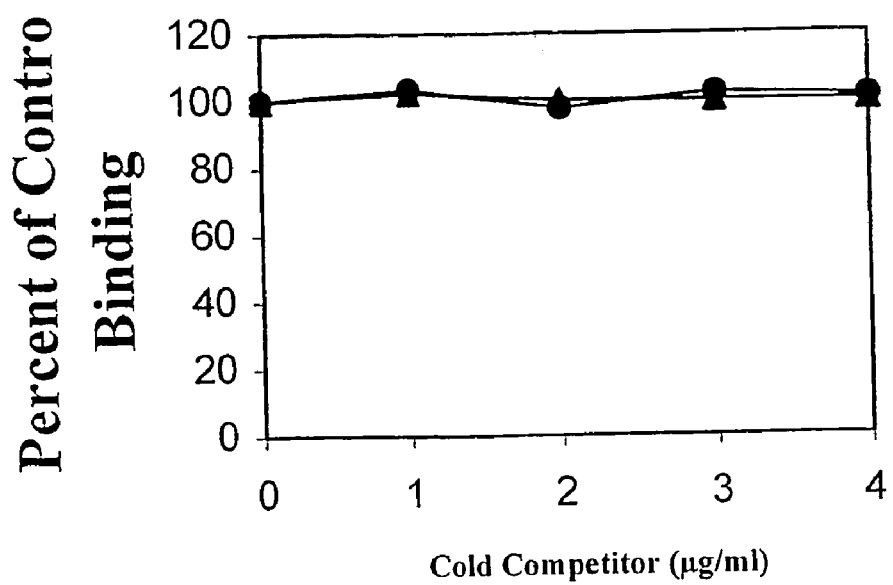
FIG. 5B shows $2.5 \times 10^4$ cells incubated with 100 ul of different concentrations (1 µg/ml, 2 µg/ml, 3 µg/ml and 4 µg/ml) of anti-SR antibody (solid triangle) or isotype control antibody (solid circle) for 1 h on ice. Cells were washed to remove excess antibody and further incubated with 50% saturating amounts of dG20-biotin (SEQ ID NO:6) for 1 h followed by Extravidin-PE for 30 min. Cells were washed and analyzed by flow cytometry.

In an effort to determine the identity of the dG20 (SEQ ID NO:6) binding proteins, Western blots were performed. Thus, NCC membrane preparations were probed with polyclonal anti-histone-1 mab by Western blot analysis. FIG. 4C demonstrates that NCC membrane lysates probed with this antibody bound to 14-18 and 29 kDa proteins. The same anti-histone antibody, however, did not block dG20 (SEQ ID NO:6) binding to NCC.

dG20 (SEQ ID NO:6) Binding Proteins on RAW264.7 Cells are not Scavenger Receptors Experiments were conducted to determine whether blocking of SR with anti-SR antibody on RAW 264.7 cells prevented dG20 (SEQ ID NO:6) binding. To accomplish this, competitive binding experiments were conducted. $2.5 \times 10^4$ cells were incubated with PAB for 1 h/4° C. followed by incubation with 100 µl of 5 µg/ml of FITC conjugated anti-SR antibody or isotype control antibody for 1 h on ice. Cells were washed twice and analyzed by flow cytometry. In FIG. 5A, SR antibody binding to RAW 264.7 cells is shown by flow cytometry. In FIG. 5B, it is shown that pre-treatment of cells with 14 µg/ml of anti-SR antibody did not inhibit binding by dG20 (SEQ ID NO:6)-biotin.

Binding of dG20 (SEQ ID NO:6) to NCC Up-Regulates Expression of Membrane Proteins Experiments were conducted to determine whether dG20 (SEQ ID NO:6) binding to NCC up-regulated (homologous) receptor protein expression. Purified NCC were incubated with dG20 (SEQ ID NO:6) for different time periods and cells were examined (by flow cytometry) for increased expression of the homologous dG20 (SEQ ID NO:6) binding proteins. In FIGS. 6A and 6B, comparisons between media control and ODN-biotin (dG20 (SEQ ID NO:6)) treatment demonstrated that there was an increase in the percentage dG20 (SEQ ID NO:6) positive NCC at 36 h (26% increase), 48 h (28% increase) and 72 h (40% increase) post-treatment (FIG. 6A). In FIG. 6B, the percentage increase of MFI of dG20 (SEQ ID NO:6) treated cells (compared to media controls) was more than 100% [(79-21)/21×100)] after 36 h and approximately 35% [(76-56)/56×100)] after 48 h treatment.

Figure 7:
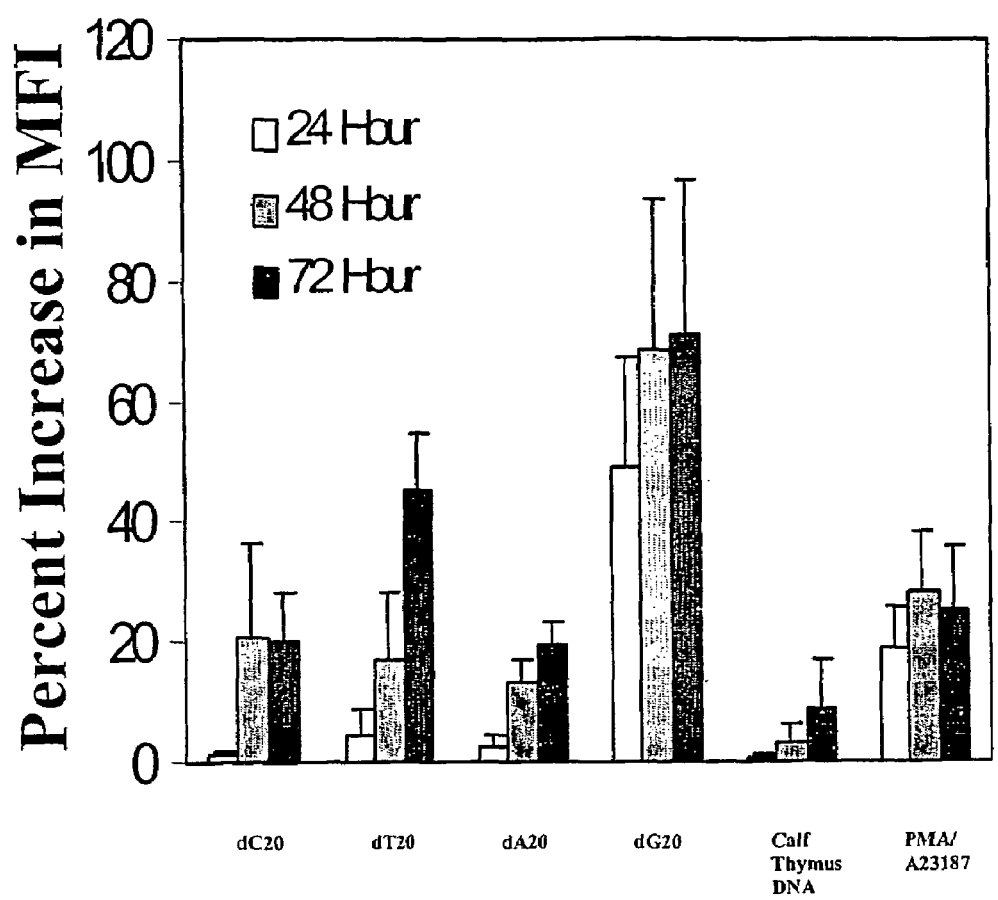
FIG. 7 shows synthetic oligodeoxynucleotides upregulate NCCRP-1 expression. Purified NCC ($1 \times 10^6$ cells/mil) were incubated with different sODNs (50 µg/ml), calf thymus DNA (5 µg/ml) and PMA/A23187 (0.5 µg/ml and 2.5 µg/ml respectively) for different time periods. At each time point, $1 \times 10^5$ cells were harvested, washed twice with PAB and stained with saturating concentrations of mab 5C6 (anti-NC-CRP-1). Analysis was done by flow cytometry. Percent increase in MFI was compared with non-treated controls. The mean±standard deviation of three independent experiments is shown.

All single base ODNs were next examined for their ability to up-regulate expression of NCCRP-1. This protein has been previously characterized as an activation/antigen receptor (Evans et al., 1988, J. Immunol. 141:324-32) and signaling protein on teleost NCC. FIG. 7 shows that dG20 (SEQ ID NO:6) produced the greatest increase in membrane expression of NCCRP-1 following 48 h and 72 h treatments. Positive and negative controls were PMA/A23197 and calf thymus DNA, respectively.

Effects of DNase-I Treatment on the Oligodeoxynucleotides

Figure 8:
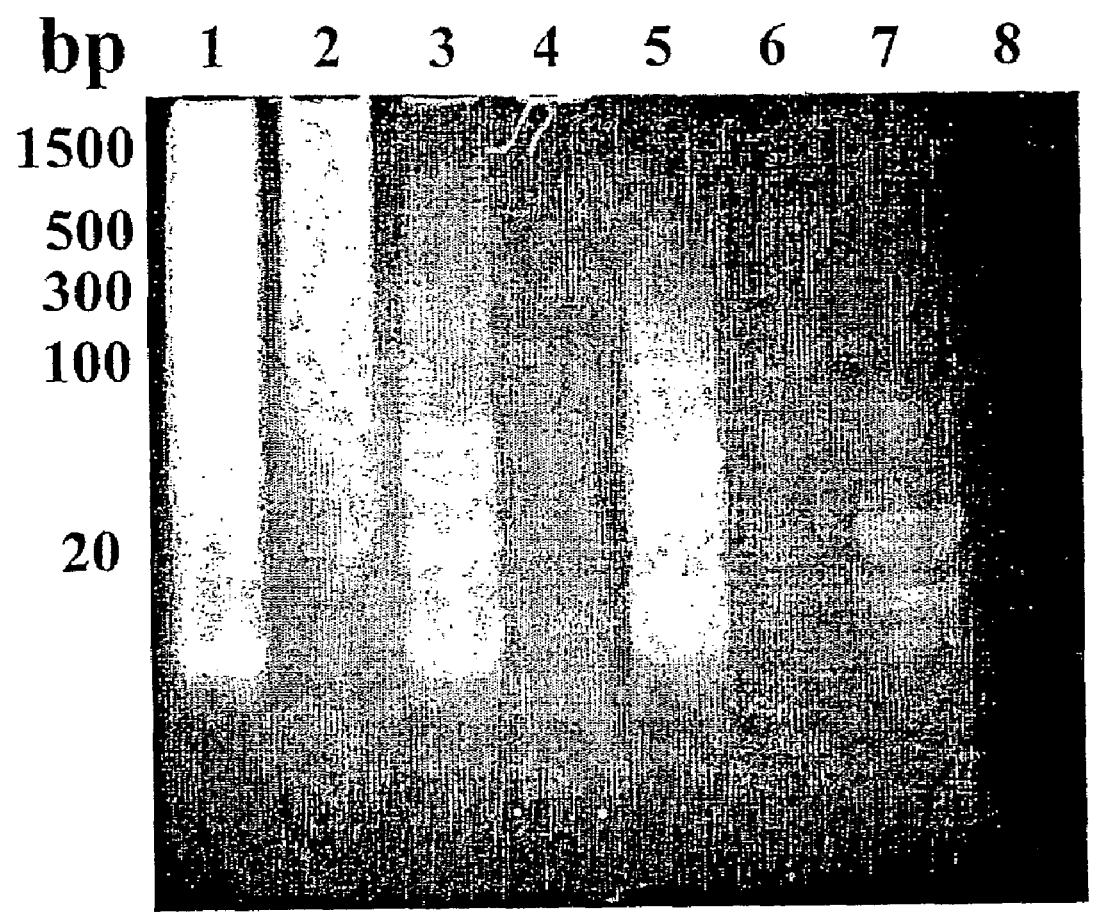
FIG. 8 shows ODN dG20 (SEQ ID NO:6) forms complexes. Equal amounts of ODNs dG20 (SEQ ID NO:6) (lane 1 and 2), dC20 (SEQ ID NO:8) (lanes 3 and 4), dA20 (SEQ ID NO:9) (lanes 5 and 6) and dT20 (SEQ ID NO:10) (lanes 7 and 8) either non-treated (lanes 1,3,5 and 7) or treated (lanes 2,4,6 and 8) with DNase I were resolved in a 15% denaturing polyacrylamide gel at 180 v for 90 min. Gel was stained with ethidium bromide (0.5 mg/ml) for 30 min at room temperature. Staining patterns were resolved using UV trans-illuminator.

One potential mechanism for dG20 (SEQ ID NO:6) binding and cellular activation may be dependent on the unique conformations (eg. G-quartet) attained by single stranded oligodeoxyguanosine that regulates binding to pattern recognition proteins. To examine the complex structural conformations of dG20 (SEQ ID NO:6), experiments were performed to determine the potential resistance of the single base ODNs to DNase fragmentation. Equal amounts of each ODN were treated with DNase I and resolved by SDS-PAGE for effects on electrophoretic mobility (e.g. residual complex formation). In FIG. 8, lanes 1, 3, 5 and 7 contain ODNs that were not treated with DNase I compared to each treated ODN in: lane 2 (dG20 (SEQ ID NO:6)), lane 4 (dC20 (SEQ ID NO:8)), lane 6 (dA20(SEQ ID NO:9)) and lane 7 (dT20 (SEQ ID NO: 10)). A difference in the intensity of ODNs stained with ethidium bromide was observed. This may be due to differential staining of different ODNs with ethidium bromide. SDS-PAGE and ethidium bromide staining demonstrated a difference in the staining profile of dG20 (SEQ ID NO:6) compared to both non-treated and DNase I treated ODNs. The DNA "smear" in lanes 1 and 2 represent relatively large molecular weight complexes of dG20 (SEQ ID NO:6) because of apparent increased resistance to DNase I treatment.

The ability of dG20 (SEQ ID NO:6) to bind and induce activation of cells may be attributed to the unique conformations (eg. G-tetrad) attained by single stranded oligodeoxyguanosine. Intrachain Hoogsteen base pairing (with parallel-strand alignment) as well as interchain base stacking of G-tetrads to form- G-quadruplexes may produce patterns that recognized by membrane proteins or PRRs. These unique bonding properties of single base ODNs may impose important immunologic/adjuvant properties on dG20 (SEQ ID NO:6) including: DNase resistance, in vivo retention without deleterious immunological consequences (i.e. induction of autoimmunity) and specific binding to cells from many different vertebrate species.

Discussion

In the instant example, single base ODNs containing dG20 (SEQ ID NO:6) were shown to specifically bind to NCC (Oumouna et al., 2002, Dev. Comp. Immunol. 26:257-69). The results disclosed in the instant example indicate that NCC from teleosts can be directly activated by CpG (SEQ ID NO:7) ODNs to induce cytolytic activity against tumor target cells. An ODN hierarchy for activation of cytotoxicity was shown: (a) ODNs composed of GpC (SEQ ID NO:11) motifs had the highest activity when followed by the sequence -AACGTT-; (b) the hexamer palindrome sequence of 5'-pu-pu-CpG-py-py-3' was also stimulatory in teleosts where 5' purines are preferably expressed as GpT and 3' pyrimidines are TpT (Oumouna et al., 2002, Dev. Comp. Immunol. 26: 257-269). DNA binding proteins on NCC also recognized polyguanosine oligodeoxynucleotides.

Example 2

Molecular Characterization of a Novel Pattern Recognition Protein from Nonspecific Cytotoxic Cells: Sequence Analysis, Phylogenetic Comparisons and Antimicrobial Activity of a Recombinant Homolog The example herein describes the identification of a novel oligodeoxynucleotide (ODN) binding membrane protein expressed by channel catfish (*Ictalurus punctatus*) NCC. Peptide fingerprinting analysis of the ODN binding protein (referred to as NCC cationic antimicrobial protein-1/NCAMP-1) identified a peptide that was used to design degenerate primers. A catfish NCC cDNA library was used as template with these primers and the PCR-amplified product was sequenced. The translated sequence contained 203 amino acids (molecular mass of 22,064.63 Daltons) with characteristic lysine rich regions and a pI=pH 10.75. Sequence comparisons of this protein indicated similarity to zebrafish (51.2%) histone family member 1-X and (to a lesser extent) to trout H1. A search of EST databases confirmed that NCAMP-1 is also expressed in various tissues of channel catfish as well as zebrafish. Inspection for signature repeats in NCAMP-1 and comparisons with histone-like peptides from different species indicated the presence of multiple lysine based motifs composed of AKKA (SEQ ID NO:24) or PKK repeats. The novel protein was cloned, expressed in *E. coli* and used to generate rabbit antiserum. The recombinant NCAMP-1 bound GpC (SEQ ID NO:11) and CpG (SEQ ID NO:7) ODNs and was detected with homologous anti-NCAMP-1 polyclonal antibodies. Western blots of NCC membranes using anti-ncamp-1 serum detected a 29 kDa protein. Binding competition experiments demonstrated that anti-ncamp-1 antibodies and GpC (SEQ ID NO:11) bound to the same protein on NCC. Two different truncated forms of NCAMP-1 as well as the full-length recombinant protein exhibited antimicrobial activity.

Materials and Methods
Media, Reagents and Antibodies

Cells were cultured in RPMI-1640 (Cellgro, Media Tech, Washington, D.C.) supplemented with L-glutamine, sodium pyuvate, MEM vitamin solution, MEM amino acid solution, MEM non-essential solution (Cellgro), 50 mg/ml gentamicin (Schering-Plough Animal health Corp., Kenilworth, N.J.) and 10% fetal bovine serum (FBS) (Atlanta Biologicals, Norcross, Ga.). PAB solution contained phosphate buffered saline with 0.1% sodium azide and 1% bovine serum albumin. Calf thymus DNA (#D-4764) and Extravidin-phycoerythhrin (PE) conjugate (#E4011) were purchased from Sigma. Cells in all assays were 70-90% mab 5C6 positive. Monoclonal antibody 5C6 (IgM isotype) specific for a 32-kDa receptor protein (i.e. NCCRP-1; 39) was prepared in-house. Anti-mouse IgM-FITC and biotin-anti-IgM conjugates were obtained from Sigma Immunochemicals. Rabbit polygonal anti-recombinant ncamp-1 was generated by the Polyclonal Antibody Production Service at the University of Georgia using standard immunization protocols with His-Tag purified NCAMP-1 protein (see below) as immunogen. The IgG fraction was isolated by Protein A agarose (IPA-300, Repligen, Cambridge Mass.) chromatography. Normal rabbit serum (NRS; E-9133, Sigma) was treated similarly for use as negative control IgG.

Oligodeoxynucleotides (ODNs)

ODNs were purchased from MWG-Biotech (High Point, N.C.). All ODNs were synthesized as a phosphodiesters. Three prime end modifications (biotin or rhodamine) were done by the manufacturer. The ODNs were: TCGTCGT-TGTCGTTGTCGTT (CpG) (SEQ ID NO:7); TGCTGCT-TGTGCTTGTGCTT (GpC) (SEQ ID NO:11); 20 mers of polyguanosine (dG20) (SEQ ID NO:6); and 20 mers of polyadenine (dA20)(SEQ ID NO:9). ODNs were resuspended in PBS prepared in endotoxin free water (#210-7, Sigma). All ODNs contained less than 0.015 EU/ml endotoxin as determined by the Limulus amebocyte lysate assay (E-Toxate Sigma).

Experimental Animals and Isolation of NCC

Channel catfish weighing 20-60 g were net captured and sacrificed by submersion in anesthetic (3-aminobenzoic acid ethyl ester; #D-5040 Sigma). Anterior kidney (AK) tissue (mammalian bone marrow equivalent) was removed aseptically and passed through screen mesh to obtain single cell suspensions in complete RPMI-1640 containing 10% FBS. Red cells were first removed by one cycle of centrifugation through Ficoll-Hypaque, (400×g/30 min/room temp). Cells were harvested and purified centrifugation over a 45.5% Percoll cushion. Cells at the interface were collected, washed once with RPMI and resuspended as indicated.

Flow Cytometry

The ability of NCC to bind was ODNs was assessed by flow cytometric analysis. Rhodamine-labelled CpG (SEQ ID NO:7) was added to purified NCC cells resuspended in PAB. Cells were incubated on ice for 45 min washed with PAB and analyzed. The surface expression on NCC of NCAMP-1 was evaluated using polyclonal rabbit IgG prepared against recombinant ncamp-1. Purified NCC in PAB was incubated with antibody or control rabbit IgG for 1 hour on ice. Cells were washed in PAB, anti-rabbit IgG FITC was added (1 hour on ice). Cells were washed in PAB and analyzed. Analysis was performed using an EPICS XL-MCL four color analyzer (Coulter Electronics Corp, Hileah, Fla.), equipped with 15 mW air cooled argon-ion laser operating at 488 run wavelength. FITC was detected using 525 nm bandpass filter by photomultiplier tube 1 (PMT1) and the rhodamine and PE signals were detected with 575 nm bandpass filter by photomultiplier tube 2 (PMT2). Data was analyzed using Coulter's System II software, version 3.0.

Competitive Binding.

Catfish NCC were purified as described previously except were subjected to two cycles of Ficol-Histopaque centrifugation prior to centrifugation on 45.5% Percoll. Purified cells were resuspended in PAB. Labeled ODNs were used as previously described (Oumouna et al., 2002, Dev. Comp. Immunol. 26:257-269). Polyclonal anti-NCAMP-1 I-G (or NRS IgG) or biotinylated ODN was added to cells and incubated for 45 minutes on ice. Cells were washed in PAB and the appropriate second reagent was added (i.e. antibody was added to cells first followed by addition of labeled ODN; or labeled ODN was added to cells first followed by the addition of antibody). Samples were incubated for 45 min on ice, washed in PAB and further incubated (45 min on ice) in either Extraviden-PE or anti-rabbit IgG FITC as indicated.

Preparation of Cell Membranes

Purified NCC were washed three times with ice cold TBS (25 mM Tris-Cl, pH 7.5, 150 mM NaCl). Cells were resuspended in Dounce homogenization buffer (10 mM Tris-Cl, pH7.6, 0.5 mM $MgCl_2$, 1 µg/ml each leupeptin, pepstatin and aprotinin; 1 mM PMSF) at $2\times10^7$ cells/ml and incubated on ice for 15 min prior to homogenization with 50-60 strokes of a Dounce homogenizer (type B pestle). Salt was adjusted to 0.15 M by the addition of tonicity restoration buffer (10 mM Tris-Cl, pH 7.6, 0.5 mM $MgCl_2$ and 0.6 M NaCl) per ml of homogenization buffer and cells were spun at 500 g for 5 min to remove nuclei. Supernatant was collected and EDTA was added to 5 mM. Supernatant was then spun at 13000 rpm for 10 min, 4C. Supernatant was discarded and the pellet was washed twice with cold TBS with protease inhibitors (as above). Membrane pellets were resuspended in hot SDS PAGE sample buffer at $2\times10^8$ cell equivalents (CE)/ml.

Southwestern (ODN) Blots

Biotinylated ODNs were used to identify potential. DNA binding proteins in NCC membrane lysate preparations and to evaluate the ODN binding of recombinant NCAMP-1.

Membrane lysates were prepared as indicated above. Purified recombinant NCAMP-1 was mixed with SDS-PAGE sample buffer (reducing) prior to electrophoresis. Samples were run in 12.5% SDS-PAGE and transferred to nitrocellulose. Membranes were blocked in Superblock (Pierce, Rockford Ill.) blocking solution with 0.05% Tween-20. ODN's were diluted in Superblock and added to membranes (1 h, room temperature). Membranes were washed (3×) in TBS with 0.5% Tween-20 (TBST). Neutraviden-HRP (Pierce) diluted in Superblock (minimum dilution 1:50000) was added and incubated for 30 min at room temperature. Blots were washed (3×) in TBST and were developed with enhanced chemiluminiscence (SuperSignal® West Pico Pierce, Rockford, Ill.).

Western Blot

Anterior kidney NCC membrane preparations were resolved on 12.5% gels and transferred to nitrocellulose for Western blot analysis. Filters was blocked for 30 minutes at room temperature (RT) with blocking buffer (5% non-fat dry milk in TBST), incubated with rabbit anti-ncamp-1 IgG (or control IgG) followed by washing and anti-rabbit IgG-Horseradish Peroxidase conjugate diluted 1:10000 in blocking buffer. Blots were developed with enhanced chemiluminescence as above.

Protein Fingerprinting, Primer Design and PCR Amplification.

Proteins identified by ODN binding in Southwestern blots were excised from Coomassie stained gels and protein fingerprinting was done by microcapillary reverse phase HPLC followed by ion trap mass spectrometry (MS) (Harvard Microchemistry facility). The MS spectra of peptide fragments were compared (using an algorithm called Sequest) and the results were manually verified by checking the fidelity of the run and biological significance. One of the peptide fragments identified had high degree of similarity to the MS spectra of a peptide fragment from histone H1 from trout. This peptide fragment was used to design degenerate primers to amplify portions of the gene (in combination with vector specific primers for the library) using cDNA library constructed from NCC purified from catfish anterior kidney as a template. The amplicons were cloned in to a pDrive TA cloning vector (Qiagen, Carlsbad, Calif.) and sequenced in a 373 A DNA sequencer (Applied Biosystems, Foster City, Calif.) at the Molecular Genetics Instrumentation Facility (University of Georgia, Athens) using the standard protocol described by the manufacturer. Sequences were compared with the known sequences in DDBJ/EMBL/GenBank databases using BLAST version 2.2.5. Based on the sequence, which had similarity to H1 histone family X members, non-degenerate primers were designed to screen the cDNA library using a directed PCR-based iterative cloning protocol. Several clones were sequenced in both directions to verify the complete sequence.

Recombinant Protein

Primers were designed to amplify the entire coding region of NCAMP-1 to generate the recombinant protein. PCR amplified and restriction digested insert DNA was directionally cloned in to pET-21 b expression plasmid (Novagen, San Diego, Calif.), which allow the expression of protein with C-terminal His-Tag. The resulting plasmid (pET-21b-ncamp) was electroporated into E. coli expression strain BL21(DE3) pLysE (Novagen). Recombinant protein was produced from bulk cultures grown till 0.6-1.0 OD and induced with 1 mM isopropyl-beta-D-thiogalactopyranoside (IPTG, #BP1620-1, Fisher, Fair Lawn, N.J.) for 3 h at 30° C. Lysates were prepared from IPTG induced cultures by sequential incubations in lysozyme (1 mg/ml), Triton X-100 (0.5%), DNaseI (5 µg/ml) and RNase A (10 µg/ml). Ncamp-1 was purified from cleared lysates using Ni-NTA-agarose (#30210, Qiagen, Valencia, Calif.) according to manufacturer's instructions. Mock (vector) lysates were by generated similarly from bacteria transformed with pET21b vector only and were "purified" on NiNTA beads for use as negative controls where indicated.

Anti-Microbial Assay with Recombinant NCAMP-1

The recombinant protein was examined for anti-microbial activity by a modified broth dilution assay. NCAMP-1 activity was tested against Gram positive (Micrococcus luteus, Streptococcus iniae) and Gram negative (E. coli, DH5alpha strain) microorganisms. S. iniae was grown and tested for susceptibility in Todd-Hewitt broth (THB) at 30° C. E. coli and M. luteus were grown and tested at 37° C. in Mueller-Hinton broth (MHB). Overnight cultures were diluted into fresh media and grown at the indicated temperature for 3-6 h. Cultures were diluted to 5000 CFUs (colony forming units)/ml in 10 mM sodium phosphate buffer (NAPB), supplemented to 10% wvith either MHB or THB. The relationship between $A_{620}$ and CFUs was previously determined in our laboratory for each bacteria. Fifty microliters of bacteria (5000 CFUs) were added to an equal volume of NCAMP-1 (or control protein) diluted in 10 mM NAPB to the indicated protein concentration. Assay tubes were incubated at the appropriate temperatures for 2 h with shaking. Colony counts were then determined by plating serial dilutions of test cultures on the appropriate media. Results are expressed as CFUs/ml.

Results

Oligodeoxynucleotide (ODN) Binding to (ICC) Membrane Proteins

Figure 9:
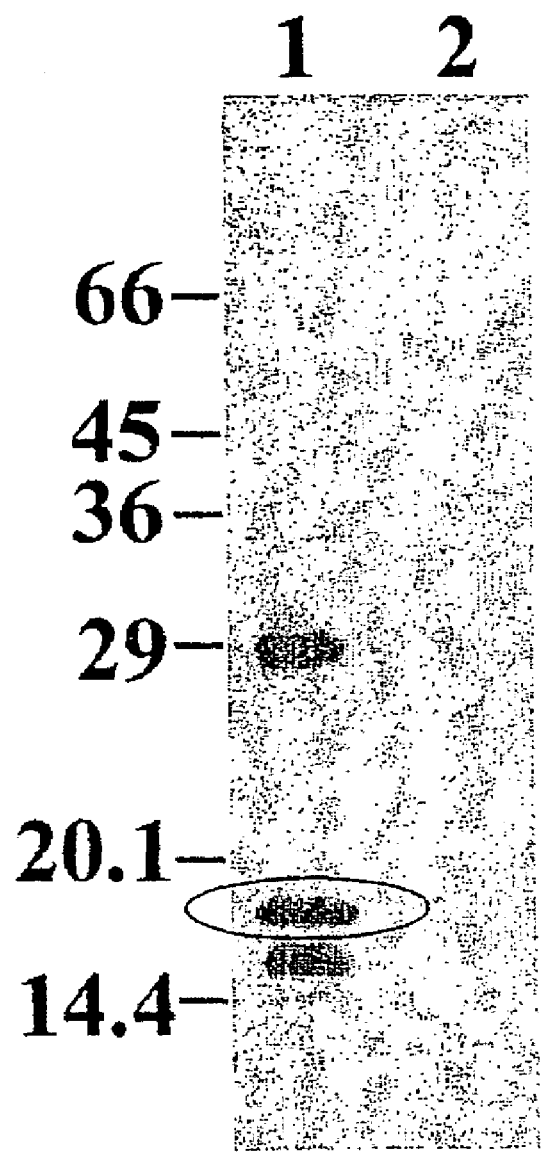
FIG. 9 shows southwestern blot analysis of membrane lysate prepared from NCC. Blots were probed with biotinylated ODN (GpC (SEQ ID NO:11)) and Extraviden-HRP (Lane 1) or Extraviden-HRP only (Lane 2). Four proteins (14, 16, 18, and 29 kDa) were identified. The 18 kDa protein was excised from Coomassie stained gels and submitted for trypsin digestion/MS analysis.

The binding activity of the ODNs were first confirmed by flow analysis of CpG (SEQ ID NO:7) binding to NCC. FIG. 9 demonstrates that CpG (SEQ ID NO:7) binds approximately 36% of purified NCC whereas conjugate control binding was less than 5%. To identify the membrane proteins that bound to the oligodeoxynucleotide, ligand (Southwestern) blots were performed using NCC membrane lysates. NCC membrane preparations were analyzed by SDS-PAGE (12.5%) and blotted onto nitrocellulose. Membranes were probed with biotinylated GpC (SEQ ID NO:11) to identify the bacterial DNA binding proteins (FIG. 9, lane 1). This ODN was previously shown (Oumouna et al., 2002, Dev. Comp. Immunol. 26:257-269) to compete with CpG (SEQ ID NO:7) for binding to NCC. Four distinct molecular weight signals were identified: 14, 16, 18 and 29 kDa. Lane 2 is the conjugate control. The 18 kDa protein was excised and sent to Harvard Microchemistry laboratory for protein processing and fingerprinting analysis.

Sequence Analysis of the DNA Binding Protein

One of the peptides identified by fingerprinting analysis had the following sequence: GASGSFKLNKK (SEQ ID NO:25). Degenerate primers were designed based on this sequence. The cDNA product obtained following PCR amplification was sequenced. This product was used to synthesize nondegenerate primers to screen an NCC cDNA library and identify individual full-length clones of the gene coding for this novel protein. The cDNA product was translated and the complete amino acid (aa) sequence was submitted to NCBI (accession numbers AAQ99138 and AY324398) and is shown in FIG. 10.

Characteristics of the DNA Binding Gene/Protein

The gene encoding the ODN binding protein shown in FIG. 10 has a typical polyadenylation signal and poly-A tail. Analysis of the open reading frame product predicted a protein of 22,064.63 Daltons containing 203 amino acids. This protein has a pI of 10.75; it contains 58 strongly basic amino acids (K, R); 55 hydrophobic amino acids (A, I, L, F, W, V); and it has 50 polar amino acids (N, C, Q, S, T, Y). A database search for other proteins with similar and/or identical sequences to this novel protein revealed that it is similar to H1 histone family X proteins from zebra fish (zf) (192 aa), xenopus (217 aa), mouse (188 aa) and human (213 aa) (FIG. 11). Amino acids 113-123 (FIG. 11) were the source for the design of the original degenerate primers. This 10 aa sequence is identical to the original identified sequence by fingerprinting analysis except for a S115N substitution. Table 3 and FIG. 11 compares the sequence obtained with H1X and H1 family members from both cold and warm blooded vertebrates.

TABLE 3

Amino acid identity of catfish DNA binding protein to other histone-like proteins.

|  | H1X | | | | H1 | |
| --- | --- | --- | --- | --- | --- | --- |
|  | Danio | Human | Mouse | Xenopus | Trout | Human |
| DBP | 51.2 | 42.4 | 43.9 | 42.9 | 30.3 | 33.1 |
| H1X: Danio | — | 44.1 | 41.3 | 42.9 | 34.7 | 33.9 |
| Human | — | — | 68.5 | 53.6 | 28.6 | 26.7 |
| Mouse | — | — | — | 50 | 26.9 | 25.1 |
| Xenopus | — | — | — | — | 26.7 | 26.6 |
| Trout | — | — | — | — | — | 61.9 |

H1XHUM: H1 histone family member X from human (Accession # BAA11018) (SEQ ID NO: 15),
H1XMUS: H1 histone family member X from mouse (Accession # XP_144949) (SEQ ID NO: 14),
H1X-Xen: H1 histone family member X from Xenopus levis (Accession # AAH41758) (SEQ ID NO: 13),
H1TRT: Histone H1 from trout (Accession # CAB37646)
H1HUM: Histone H1 from human (Accession # P10412).

A search of the zebrafish sequences in the NCBI database revealed a 51% similarity to the catfish NCAMP-1 protein. Table 4 and FIG. 11 compares the sequence of the zebrafish protein to other histone-like proteins.

TABLE 4

Amino acid identity of NCAMP-1-like protein in zebrafish to other histone-like proteins.

|  | NCAMP-1 | H1XHUM | H1XMUS | H1X-Xen | H1TRT | H1HUM |
| --- | --- | --- | --- | --- | --- | --- |
| Danio NCAMP-like (AAH47192) | 51.2 | 44.1 | 41.3 | 42.9 | 34.7 | 33.9 |

H1XHUM: H1 histone family member X from human (Accession # BAA11018) (SEQ ID NO: 15),
H1XMUS: H1 histone family member X from mouse (Accession # XP_144949) (SEQ ID NO: 14),
H1X-Xen: H1 histone family member X from Xenopus levis (Accession # AAH41758) (SEQ ID NO: 13),
H1TRT: Histone H1 from trout (Accession # CAB37646)
H1HUM: Histone H1 from human (Accession # P10412).

Phylogenetic Analysis of the Novel Catfish Protein

Phylogenetic analysis confirmed the comparisons shown in Table 3 and 4. The catfish ODN binding protein clustered with zebrafish and xenopus histone 1x (FIG. 12), showed a secondary similarity with mouse and human histone 1x, but was not related to any of the core histones (H2A, 2B, etc.). The tree was derived by parsimony analysis, with Mega version 2. Numbers shown above the branches are bootstrap values based upon 1000 replicates for parsimony. A separate analysis using maximum likelihood and neighbor joining methods produced a tree with similar topology. The tree was rooted on a sub-tree containing histone H2 and similar proteins.

Recombinant Expression of the 22,064 Dalton Membrane Protein

Figures 13A, 13B:
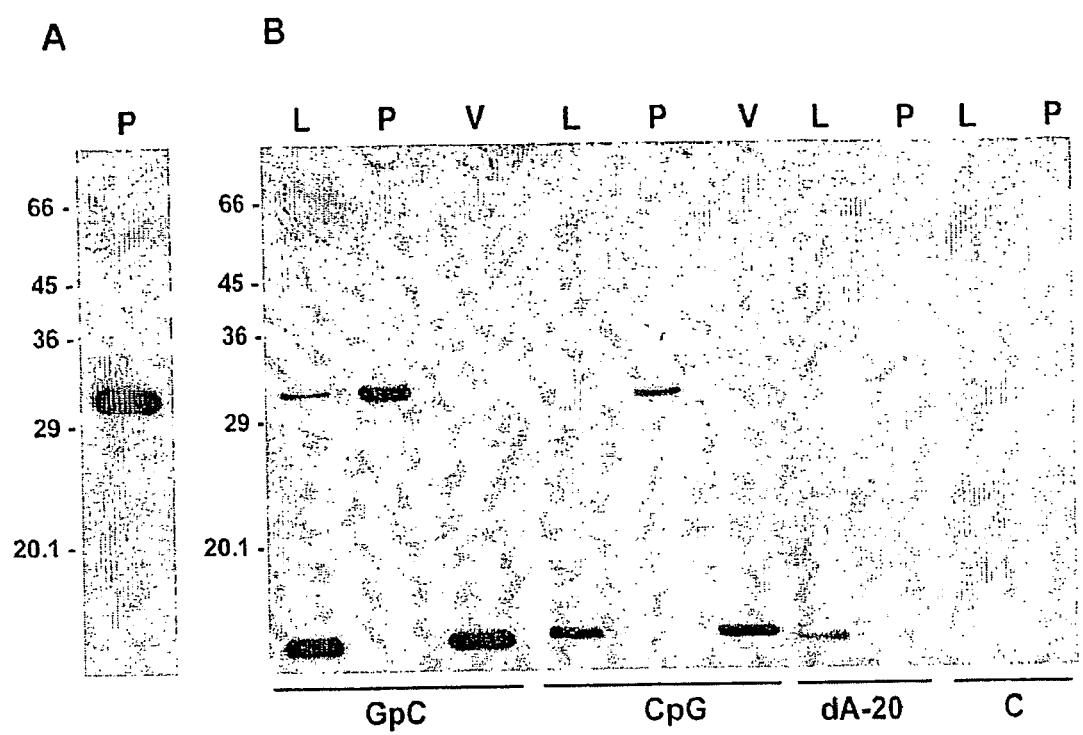
FIG. 13A shows the purified recombinant NCAMP-1 migrated at approximately 31 kDA when probed with His-Probe HRP.
FIG. 13B shows Southwestern blot analysis of binding of the purified (P) recombinant NCAMP-1 by both biotinylated GpC (SEQ ID NO:11) and CpG (SEQ ID NO:7), minimally by biotinylated polyadenine (dA20 (SEQ ID NO: 9) and Extraviden-HRP (Control). L: whole cell *E. coli* lysate prior to purification; and V: NiNTA column eluate from vector only transformed lysate treated the same as L and P.

The ODN binding protein DNA containing 6x histidines (His-tag) was cloned into pET21b by standard techniques and the resulting plasmid was transformed into E. coli as described in Materials and Methods. In FIG. 13A, purified recombinant NCAMP-1 (containing the His-Tag) was identified with the INDIA His probe-HRP. In FIG. 13B recombinant NCAMP-1 from E. coli lysates was shown by Southwestern blotting to bind to GpC (SEQ ID NO:11) and CpG (SEQ ID NO:7) (lanes 2 and 5, respectively). dA20 (SEQ ID NO:9) was used as a negative control (lanes 7 and 8).

Specificity of a Polyclonal Anti-Recombinant NCAMP-1

Figures 14A, 14B:
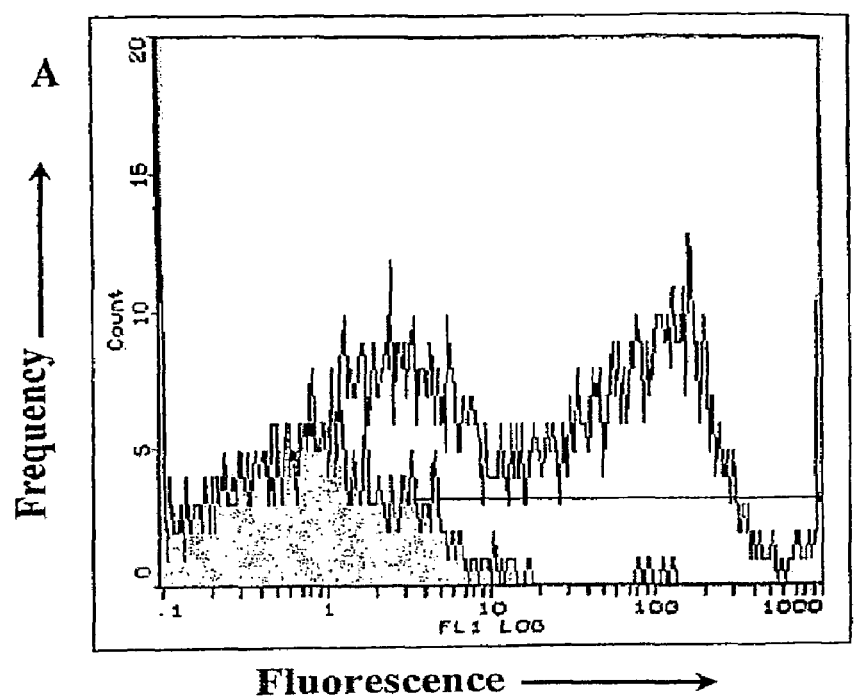
FIG. 14A shows purified NCCs incubated with anti-NCAMP-1 IgG (open histogram) or control rabbit IgG (shaded histogram) and anti-rabbit IgG FITC. Cells within the cursor were considered positive and were 53% of the total.
FIG. 14B shows blots of NCC membrane lysates probed with anti-ncamp-1 IgG (Lane 1), control rabbit IgG (Lane 2) or anti-rabbit IgG HRP only.

A polyclonal anti-serum was generated against the recombinant ncamp-1. FIG. 14A is the flow analysis of polyclonal anti-NCAMP-1 binding to purified NCC. Approximately 53% of NCC constitutively express NCAMP-1. The closed histogram is binding by rabbit pre-immune serum. The polyclonal antiserum also identified a 29 kD protein in a Western blot of NCC membrane lysates (FIG. 14B).

Reciprocal Competition Binding

Figures 15A, 15B:
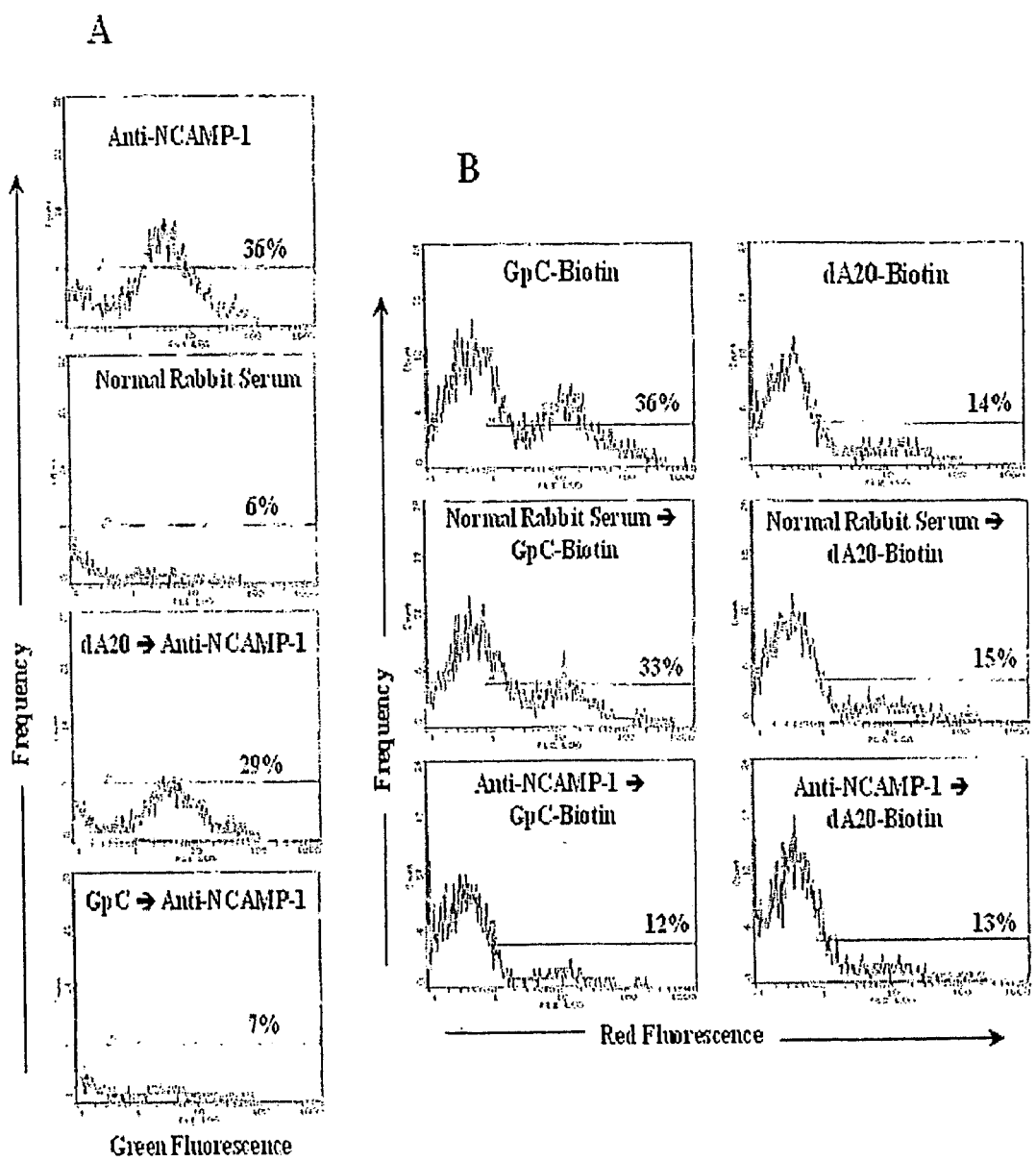
FIG. 15A demonstrates that GpC-Biotin (SEQ ID NO:11) but not dA20-Biotin (SEQ ID NO:9) inhibited binding by polygonal anti-NCAMP-1.
FIG. 15B shows that GpC (SEQ ID NO:11) competitively inhibited binding by anti-NCAMP-1 to NCC.

In order to confirm that the cloned catfish protein was indeed one of the NCC membrane proteins responsible for ODN binding, binding competition experiments between polyclonal antiserum and labeled GpC (SEQ ID NO:11) were performed with purified NCC. The flow cytometry histograms in FIG. 15 show that preincubation of purified NCC with GpC (SEQ ID NO:11) prevents sequential binding of the polyclonal serum and vice versa.

Expression of a Lysine Based Motif and Comparison with Histone-Like Proteins from Other Vertebrate Species The similarity between the N-terminus of ncamp-1 and three different antimicrobial H1 peptides is shown in FIG. 16. The most striking feature of each sequence is the predominance of lysine, alanine and proline as contiguous sequences or as xAKx, xKAKxx or xKKAx motifs. These motifs are frequently boxed by lysine (e.g. KxxxK). An algorithm would suggest that these lysine boxed motifs (LBM) may be responsible for ligand binding and/or antimicrobial functions. Similar comparisons of the LBM in the C-terminal 60 aa of NCAMP-1 with core and linker histone peptides confirmed this relationship and emphasized that although there are no sequence identities, that the similarities in expression of the LBM may impose important biological consequences.

Antimicrobial Effects of Recombinant ncamp-1

Figure 17A:
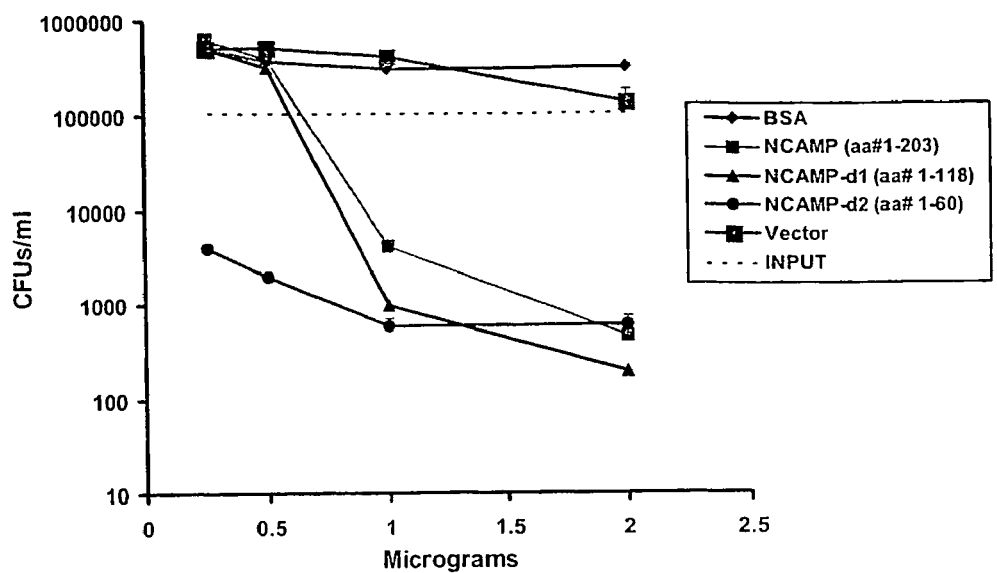
FIG. 17 shows effects of full length and truncated recombinant NCAMP-1 on *E. coli* and *Streptococcus iniae* viability. The bacteria were prepared and recombinants were expressed as described in the Materials and Methods of Example 2. The micrograms recombinant shown represent that amount in 100 μl treatment volume and the dotted line indicates initial number of bacteria added to the treatment wells.
Figure 17B:
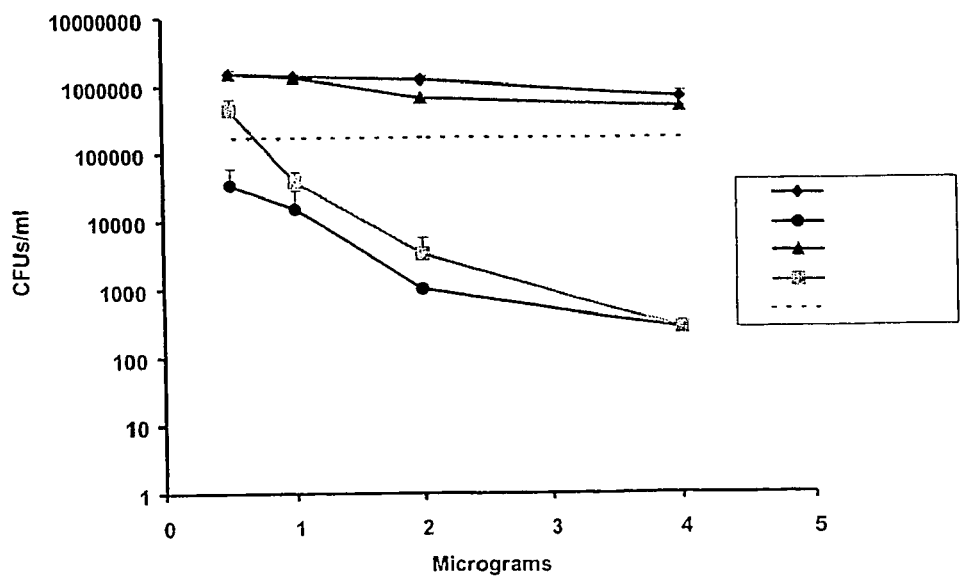

Studies were next carried out to evaluate the bactericidal activity of NCAMP-1. FIG. 17 demonstrates that both E. coli and S. iniae were killed by the full length recombinant NCAMP-1. In addition, truncated forms of NCAMP-1 were also tested and are shown in FIG. 17A and Table 5. Two different truncated recombinants (NCAMP-d1 and NCAMP-d2) killed *E. coli* at MIC$_{50}$ concentrations of 0.63 µM and 1.0 µM respectively.

TABLE 5

Minimal inhibitory concentrations for 50% bactericidal activity for full length and truncated ncamp-1.

| Species | Protein/Peptide | $^1$MIC$_{50}$ |
|---------|----------------|----------------|
| *E. coli* | NCAMP-1, aa 1-203 | 0.43 uM (SEQ ID NO: 3) |
|  | NCAMP-d1, aa 1-118 | 0.63 uM |
|  | NCAMP-d2, aa 1-60 | 1.0 uM |
| *S. iniae* | NCAMP-1, aa 1-203 | 0.86 uM |

$^1$MIC for 50% bactericidal activity.

*M. luteus* were killed by full length recombinant NCAMP-1. Cells (*M. luteus*) were grown overnight at 37° C. in Mueller-Hinton (MH) broth. Overnight cultures (500 ul) were diluted 1:100 in fresh broth and incubated for 2 hours at 37° C. After 2 hours, the OD$_{620}$ was measured. Using a previously determined relationship of OD$_{620}$ 0.1=1.2×10$^7$ CFUs/ml, bacteria was diluted to 10$^5$ CFUs/ml in sodium phosphate buffer (pH8) supplemented with 10% with MH broth (assay buffer). The indicated proteins or assay buffer (media control) were mixed with 5000 CFUs (in triplicate) in a final volume of 100 ul and incubated at 37 C for 2 h with shaking. Serial dilutions of each sample were plated onto MH agar plates and residual colony counts were determined. Colony counts were determined after overnight incubations at 37° C. and were expressed as a percent of control (media) growth. Data shown are representative of at least 3 different experiments.

Discussion

It has previously been shown (Oumouna et al., 2002, Dev. Comp. Immunol. 26:257-269) that teleost NCC bind oligodeoxynucleotides. The studies disclosed in the instant example indicate that this binding is receptor mediated. Competition binding experiments demonstrated that CpG (SEQ ID NO:7) and GpC (SEQ ID NO:11) bound to the same receptor on NCC. The fact that scavenger receptors are not known to bind either CpG (SEQ ID NO:7) or GpC (SEQ ID NO:11) (Kaur et al., 2003, Fish Shellfish Immunol., 15:169-181) and that membrane expression of TLR9 protein has not previously been described for fish cells (Jault et al., 2004, Mol. Immunol., 40: 759-771; Meijer et al., 2004, Mol. Immunol., 40: 773-783) [although a full length TLR-like sequence has been reported for a goldfish macrophage cell line; Stafford et al., 2003, Dev. Comp. Immunol. 27: 685-698), we hypothesized that NCC might express a novel class of binding protein(s) responsible for this activity. In the present study a new DNA binding receptor with molecular similarities (less than 50% at the aa level) to histone 1x (FIG. 10) was identified. A search of the zebrafish sequences in the NCBI database revealed a similar protein, but with "unknown" functions (accession number AAH47192). The zebrafish protein has 51% similarity to the novel catfish protein (Table 4). Expression of the catfish DNA binding protein in other hematopoietic cell lines and tissues was verified by searching a channel catfish EST database and this gene expression was reported in the NK like cell line MLC-52-1 (accession numbers CB937576 and CB937396), brain (accession number BM495146) and in the anterior kidney (accession number BE469379).

Figure 12:
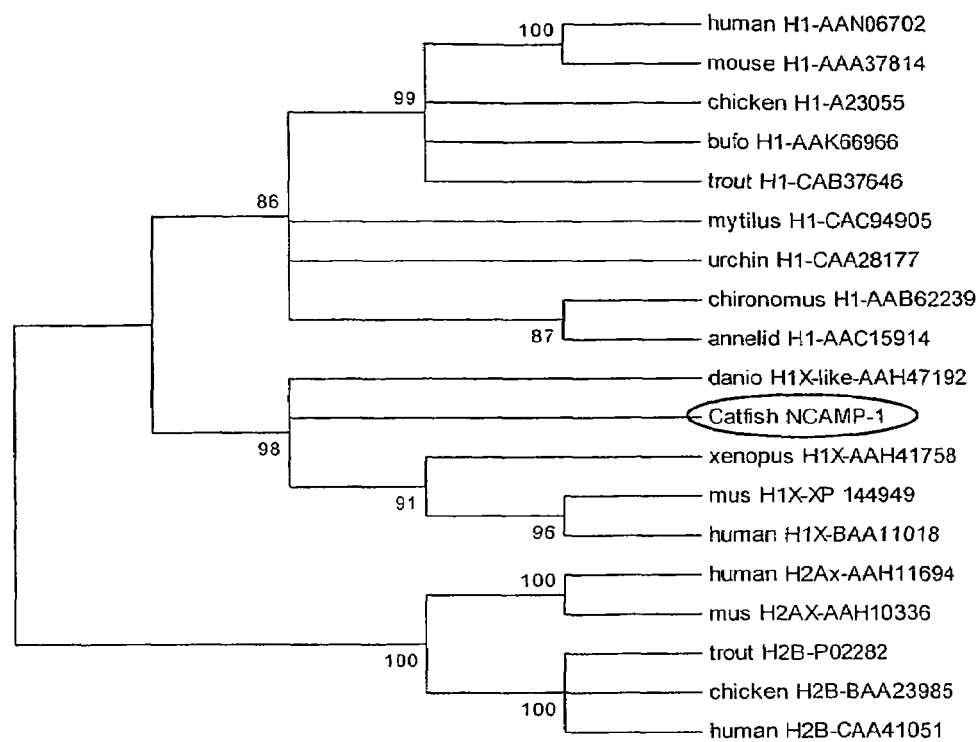
FIG. 12 show phylogenetic analysis of catfish NCAMP-1, a phylogram showing relationships of catfish NCAMP-1 to other histone-like proteins.

The NCAMP-1 gene does not have introns. The phylogenetic analysis of the ncamp-1 with other histone-like proteins indicated that this protein could be a separate evolutionary branch from the histone-like protein family (FIG. 12). Although ncamp-1 appeared related to the histone family, more closely to H1 histone family X members, this relationship was based on similarities in the conserved central domains in these proteins.

Ncamp-1 was next examined for unique domain configurations, amino acid repeats or presence of conserved motifs. The periodic expression of lysine residues with boxed nonlysine spacer amino acids indicated the presence of a novel motif. The multiple lysines are repetitively arranged in boxes characterized by: KxxxK, KKxxK and KxxKK) with an apparent "preference" for alanine and proline for spacer amino acids. We refer to these repeats as lysine-rich motifs or lysine box motifs (LBMs). Because of the similar relationship of the new protein with histone 1x proteins from other vertebrates, we next determined whether the LBMs were conserved in any phylogenetic relationship with other proteins/peptides. In Table 6, LBMs were identified in several low mw peptides that have been previously shown to have antimicrobial activity. For comparative purposes, ncamp-1 was divided into three portions/peptides each containing regions of increased expression of LBMs (i.e. ncamp-1.1,-1.2 and -1.3). In Table 6, five non-histone antimicrobial peptides (AMP) and nine histone-like peptides from phylogenetically diverse species (e.g. bacteria to human) are compared with ncamp-1 peptides for expression and frequency of LBM repeats.

TABLE 6

Lysine box motifs, anti-microbial peptides and phylogeny.
The expression and frequency of LBMs by AMP from diverse species is compared with three peptides from ncamp-1.

| Antimicrobial Peptides | # of LBMs | Species | Accession # |
|------------------------|-----------|---------|-------------|
| Bacteriocin: AYSLQMGATAIKQVKKLFKKW (SEQ ID NO: 26) | 2 | Bacteria | P80214 |
| Cecropin A: PKWKLFKKIEKVGQNIRDGIIKAGPAVA (SEQ ID NO: 27) | 2 | Moth | M63845 |
| Cupiennin: FKFLAKKVAKTVAKQAAKQGAK (SEQ ID NO: 28) | 5 | Spider | P82358 |
| NCAMP-1.1: GPASKAKPASAEKKNKKKKGKGPGKY (amino acids 27-51 of SEQ ID NO: 3) | 4 | Catfish | AY324395 |
| NCAMP-1.2: PRKTAKPTKKPAKKAAKKKKRVSG (amino acids 136-159 of SEQ ID NO: 3) | 4 | Catfish | AY324395 |

TABLE 6-continued

Lysine box motifs, anti-microbial peptides and phylogeny.
The expression and frequency of LBMs by AMP from diverse
species is compared with three peptides from ncamp-1.

| Antimicrobial Peptides | # of LBMs | Species | Accession # |
|---|---|---|---|
| NCAMP-1.3: PKKADKSPAVSAKKASKPKKAKQTKKTAKKT (amino acids 173-203 of SEQ ID NO: 3) | 3 | Catfish | AY324395 |
| H1-Trt: AEVAPAPAAAAPAKAPKKKAAAKPKK (SEQ ID NO: 23) | 2 | Trout | |
| H1-Trt: KAVAAKKSPKKAKKPAT (SEQ ID NO: 18) | 2 | Trout | |
| H2B-Trt: PDPAKTAPKKGSKKVTKXA (SEQ ID NO: 20) | 3 | Trout | |
| H2A-CF: KGRGKQGGKVRAKAKTRSS (SEQ ID NO: 19) | 3 | Catfish | |
| H1-Trt: AEVAPAPAAAAPKAPKKA (amino acids of SEQ ID NO: 23) | 1 | Trout | |
| H2B-Bass1: PEPAKSAPKKGSKKAVT (SEQ ID NO: 21) | 3 | Sea Bass | |
| H2B-Bass2: PDPAPKTAPKKGSKKAVTKTAG (SEQ ID NO: 22) | 4 | Sea Bass | |
| Buforin I: AGRGKQGGKVRAKAKTRSSRAG (SEQ ID NO: 29) | 2 | Toad | X011064 |
| Magainin II: GIGKFLHSAKKFGKAFVGEIMNS (SEQ ID NO: 30) | 1 | Frog | A29771 |
| H2B/H3-Hum: KAPRKQLATPEPAKSAPAPKKGXKKXVTKA (SEQ ID NO: 31) | 4 | Human | |
| H1-Human: KLNKKAASGEAKPKAKAKSPKKAKA (SEQ ID NO: 17) | 4 | Human | |

Comparisons demonstrated that there were essentially no sequence identities between peptides, however there were striking similarities in expression of LBMs. From 1-5 LBM repeats were found in these antimicrobial peptides. Examples of other AMP not shown but that also expressed multiple LBMs are adenoregulin from the leaf frog (*Phyllomedusa bicolor:* containing LBMs; accession #P31107) and brevinin-2E (containing 2 LBMs; accession #S33730) from the European frog (*Rana esculenta*).

A recombinant form of NCAMP-1 was expressed in *E. coli* and tested for binding to ODNs. The purified histidine-tagged recombinant protein had an apparent mw of 29-30 kDa identified by Western blot examination using His-Probe HRP (FIG. 13). The apparent mw discrepancy is produced by the abundant lysine residue content of this protein. This phenomenon has been previously reported for other histone-like AMP (Hiemstra et al., 1993, Infect. Immun. 61:3038-3046) that have a lower computed molecular weight compared to their (experimental) electrophoretic mobilities.

The novel protein, NCAMP-1 has been identified on catfish and tilapia NCC as well as on mouse and human cells. This protein participates as a positive immunoregulator during bacterial infections and provides an important and necessary effector function in the survival of vertebrate species.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosure of which are incorporated by reference in their entireties.

What is claimed is:

1. An isolated antimicrobial non-scavenger Receptor A, non-toll like receptor polypeptide optionally having a molecular weight of about 22 kD to about 30 kD and having properties selected from the group consisting of (a) comprising an amino acid sequence selected from the group consisting of (i)
(amino acid residues 1-60 of SEQ ID NO: 3);
MSAQAEETAPEAAAPVQPSQPAAKKKGPASKAKPASAEKKNKKKKGKGPG

KYSQLVINAI (ii)
(amino acid residues 1-118 of SEQ ID NO: 3);
MSAQAEETAPEAAAPVQPSQPAAKKKGPASKAKPASAEKKNKKKKGKGPG

KYSQLVINAIQTLGERNGSSLFKIYNEAKKVNWFDQQHGRVYLRYSIPAL

LQNDTLVQVKGLGANGSF (iii)
(amino acid residues 27-51 of SEQ ID NO: 3);
GPASKAKPASAEKKNKKKKGKGPGKY (iv)
(amino acid residues 136-159 of SEQ ID NO: 3)
PRKTAKPTKKPAKKAAKKKKRVSG
and (v)
(amino acid residues 173-203 of SEQ ID NO: 3);
PKKADKSPAVSAKKASKPKKAKQTKKTAKKT (b) being a polypeptide depicted in SEQ ID NO:3;
(f) being a polypeptide depicted in SEQ ID NO:3 with conservative amino acid substitutions and
(g) being a fragment of (a)-(f), wherein said fragment comprises at least 24 contiguous amino acids and antimicrobial activity.

2. A pharmaceutical composition comprising the polypeptide of claim 1 and a pharmaceutically acceptable carrier or excipient.

3. A pharmaceutical composition comprising the polypeptide of claim 1 for use in treating a disorder resulting from a microbial infection and/or reducing antibiotic resistance.

4. The pharmaceutical composition of claim 2, wherein said polypeptide is present in an amount effective to inhibit microbial growth, e.g., bacterial, protozoa, fungal growth in a subject, e.g., mammal (human) subject or in an amount effective to reduce antibiotic resistance.

* * * * *